United States Patent
Gilliland, III et al.

(10) Patent No.: US 10,661,251 B2
(45) Date of Patent: May 26, 2020

(54) CARBON BASED MATERIALS AS SOLID-STATE LIGANDS FOR METAL NANOPARTICLE CATALYSTS

(71) Applicant: Virginia Commonwealth University, Richmond, VA (US)

(72) Inventors: Stanley Eugene Gilliland, III, North Chesterfield, VA (US); Bernard Frank Gupton, Richmond, VA (US); Caleb June Kong, Richmond, VA (US); Brian Raymond Clark, Richmond, VA (US)

(73) Assignee: Virginia Commonwealth University, Richmond, VA (US)

( * ) Notice: Subject to any disclaimer, the term of this patent is extended or adjusted under 35 U.S.C. 154(b) by 0 days.

(21) Appl. No.: 16/201,222

(22) Filed: Nov. 27, 2018

(65) Prior Publication Data

US 2019/0105635 A1    Apr. 11, 2019

Related U.S. Application Data

(63) Continuation of application No. PCT/US2018/054608, filed on Oct. 5, 2018.

(60) Provisional application No. 62/568,942, filed on Oct. 6, 2017.

(51) Int. Cl.
| | |
|---|---|
| *B01J 23/42* | (2006.01) |
| *B01J 21/18* | (2006.01) |
| *B01J 37/34* | (2006.01) |
| *C07F 7/08* | (2006.01) |
| *B01J 37/02* | (2006.01) |
| *B01J 37/03* | (2006.01) |
| *B01J 35/00* | (2006.01) |
| *B01J 37/16* | (2006.01) |
| *B01J 23/44* | (2006.01) |

(52) U.S. Cl.
CPC ............ *B01J 23/42* (2013.01); *B01J 21/18* (2013.01); *B01J 23/44* (2013.01); *B01J 35/002* (2013.01); *B01J 35/006* (2013.01); *B01J 35/0013* (2013.01); *B01J 37/0201* (2013.01); *B01J 37/0236* (2013.01); *B01J 37/035* (2013.01); *B01J 37/16* (2013.01); *B01J 37/346* (2013.01); *C07F 7/0801* (2013.01); *C07F 7/0829* (2013.01)

(58) Field of Classification Search
CPC .... B01J 21/18; B01J 35/0013; B01J 37/0201; B01J 37/0236; B01J 37/035; B01J 37/346; C07F 7/0801
USPC ...................................................... 549/215
See application file for complete search history.

(56) References Cited

U.S. PATENT DOCUMENTS

| | | | | |
|---|---|---|---|---|
| 6,100,408 A | * | 8/2000 | Monkiewicz | ......... C07F 7/1876 549/215 |
| 8,871,171 B2 | | 10/2014 | El-Shall et al. | |
| 9,768,355 B2 | | 9/2017 | El-Shall | |
| 2006/0137817 A1 | * | 6/2006 | Ma | .......................... B01J 21/185 156/296 |
| 2015/0087498 A1 | * | 3/2015 | El-Shall | ................. B01J 19/126 502/5 |

OTHER PUBLICATIONS

Fitzer, Pure & Appl. Chem. 1995, 67, 473-506. (Year: 1995).*
Kong; Chem. Commun., 2018, 54, 13343-13346 ,with supplemental material. (Year: 2018).*
Galeandro-Diamant; Chem. Commun., 2015, 51, 16194-16196. (Year: 2015).*
Zhu; ACS Catal. 2018, 8, 10004-10011. (Year: 2018).*
Bandari; Catal. Sci. Technol., 2012, 2, 220-226. (Year: 2012).*
Li; RSC Adv., 2017, 7, 50729-50738. (Year: 2017).*
Gilliland; Applied Catalysis A, General 550, 168-175, 2018. (Year: 2018).*
Regalbuto, "13: Strong Electrostatic Adsorption of Metals onto Catalyst Supports." Catalyst Preparation: Science and Engineering (Apr. 19, 2016). (Year: 2016).*
Search Report and Written Opinion for International Application PCT/US2018/054608, dated Jan. 15, 2019. (Year: 2019).*
Dai; Organic Chemistry: An Indian Journal 2005, 1, 44-46. (Year: 2005).*
"Publication Details" for document with DOI: 10.1039/C8CC07641C, Retrieved Jun. 19, 2019 from https://pubs.rsc.org/en/content/articlelanding/2018/cc/c8cc07641c#!divAbstract (Year: 2019).*
Hany A Elazab et al. "Microwave-assisted synthesis of palladium nanoparticles supported on copper oxide in aqueous medium as an efficient catalyst for Suzuki cross-coupling reaction" Adsorption Science & Technology, 2018, vol. 36(5-6) 1352-1365.
Pei Tang et al. "The microwave adsorption behavior and microwave-assisted heteroatoms doping of graphene-based nano-carbon materials", Scientific Reports, 4:5901, Aug. 11, 2014.

(Continued)

*Primary Examiner* — Daniel R Carcanague

(74) *Attorney, Agent, or Firm* — W&C IP

(57) ABSTRACT

High activity metal nanoparticle catalysts, such as Pd or Pt nanoparticle catalysts, are provided. Adsorption of metal precursors such as Pd or Pt precursors onto carbon based materials such as graphene followed by solventless (or low-solvent) microwave irradiation at ambient conditions results in the formation of catalysts in which metal nanoparticles are supported on i) the surface of the carbon based materials and ii) in/on/within defects/holes in the carbon based materials.

23 Claims, 18 Drawing Sheets

(56) References Cited

OTHER PUBLICATIONS

Vadahanambi Sridhar et al. "Defect-Engineered Three-Dimensional Graphene-Nanotube-Palladium Nanostructures with Ultrahigh Capacitance", Article, ACSNANO, vol. 6, No. 12, 10562-10570, 2012.

Jian Zhang et al. "Microwave-Assisted Synthesis of Pd Nanoparticles and Catalysis Application for Suzuki Coupling Reactions", The Open Materials Science Journal, 2017, 11, 1-8.

Hassan M. A. Hassan et al. "Microwave synthesis of graphene sheets supporting metal nanocrystals in aqueous and organic media", Journal of Materials Chemistry, 2009, 19, 3832-3837.

Yu-Xi Huang et al. "Reduced Graphene Oxide Supported Palladium Nanoparticles via Photoassisted Citrate Reduction for Enhanced Electrocatalytic Activities", ACS Applied Materials & Interfaces, 2014, 6, 15795-15801.

Ning Liu et al, "Microwave-assisted synthesis of MoS2/graphene nanocomposites for efficient hydrodesulfurization", Fuel 119, Elsevier, 2014, 163-169.

Ali R. Siamaki et al, "Microwave-assisted synthesis of palladium nanoparticles supported on graphene: A highly active and recyclable catalyst for carbon-carbon cross-coupling reactions", Journal of Catalysis 279, Elsevier, 2011, 1-11.

Wenya Xu et al. "Low-temperature plasma-assisted preparatin of graphene supported palladium nanoparticles with high hydrodesulfurization activity", Journal of Materials Chemistry, 2012, 22, 14363-14368.

\* cited by examiner

Figure 6A
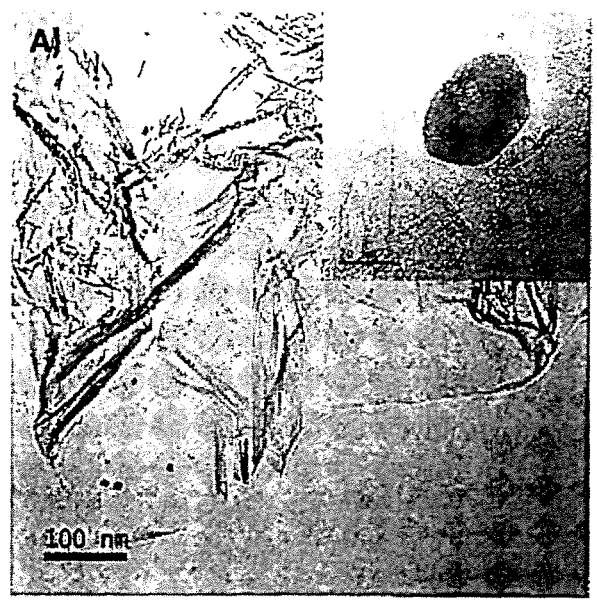
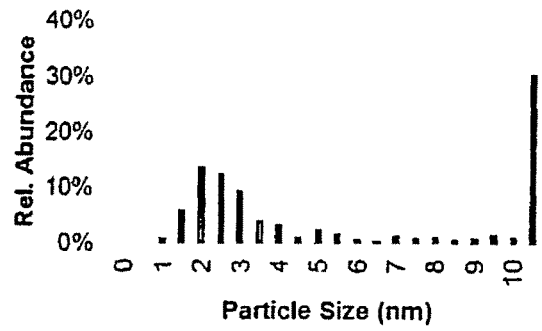
Figure 6B
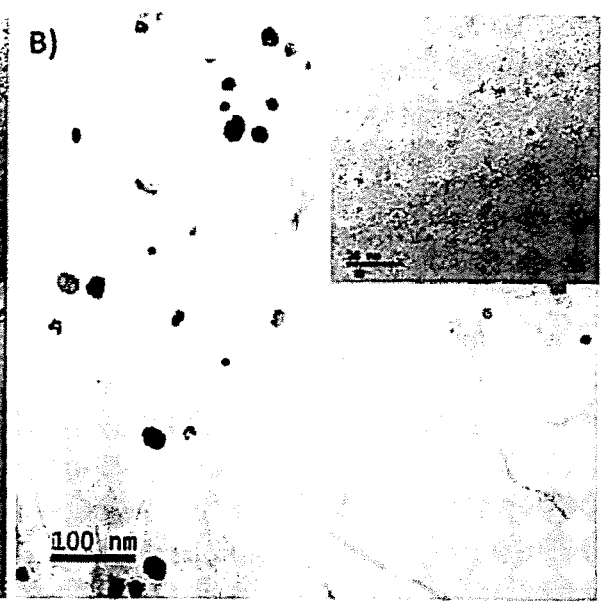
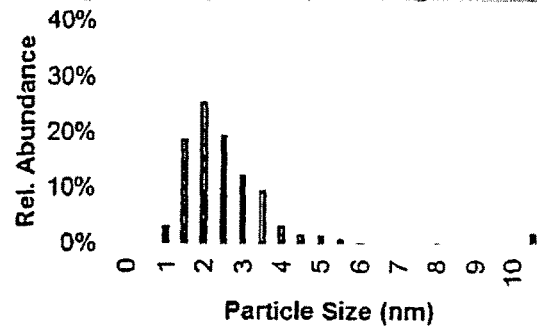

Figure 8A
Figure 8B
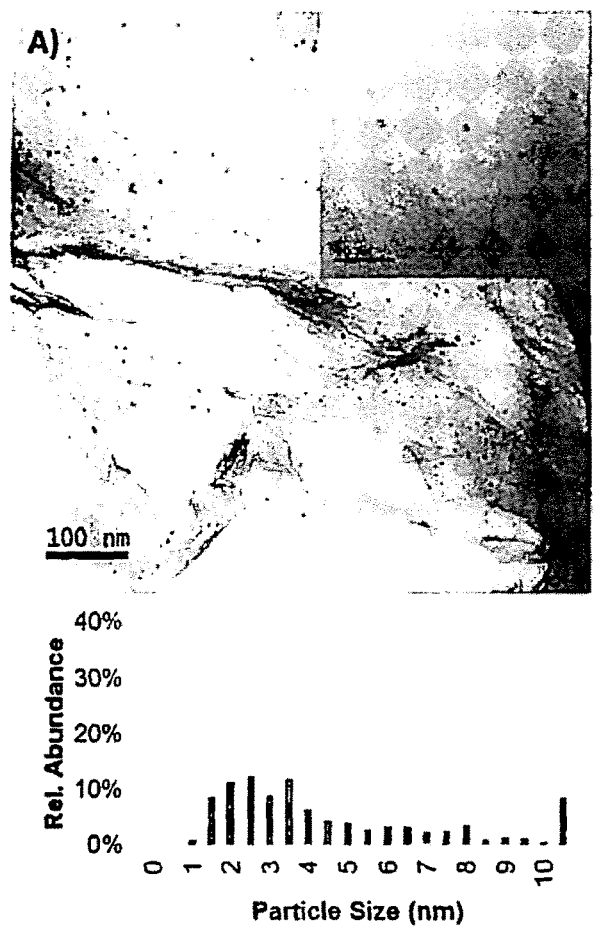
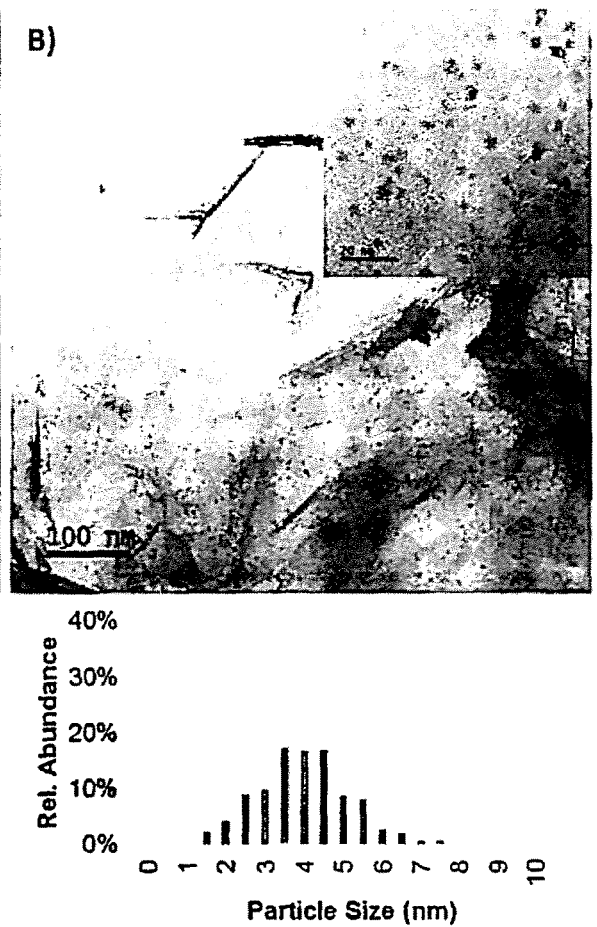

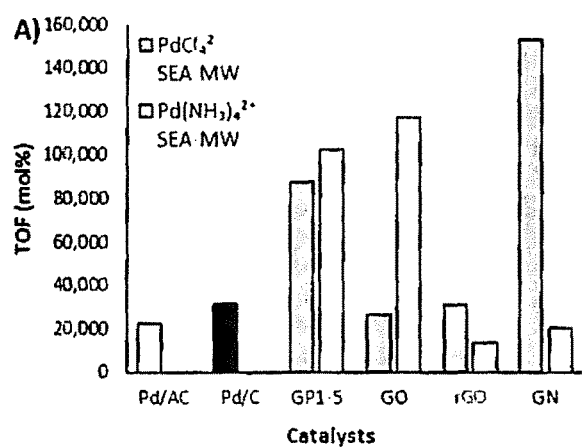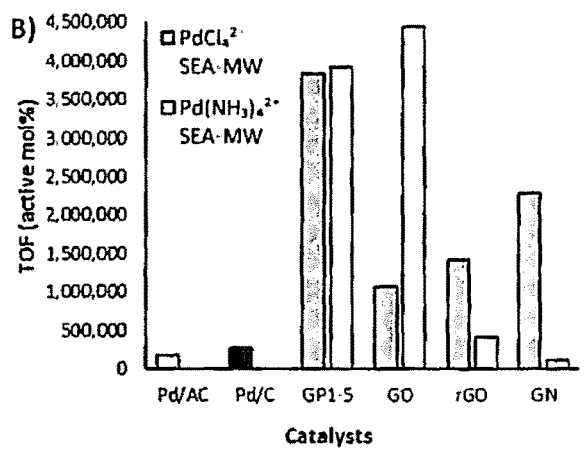
Figure 13A                    Figure 13B

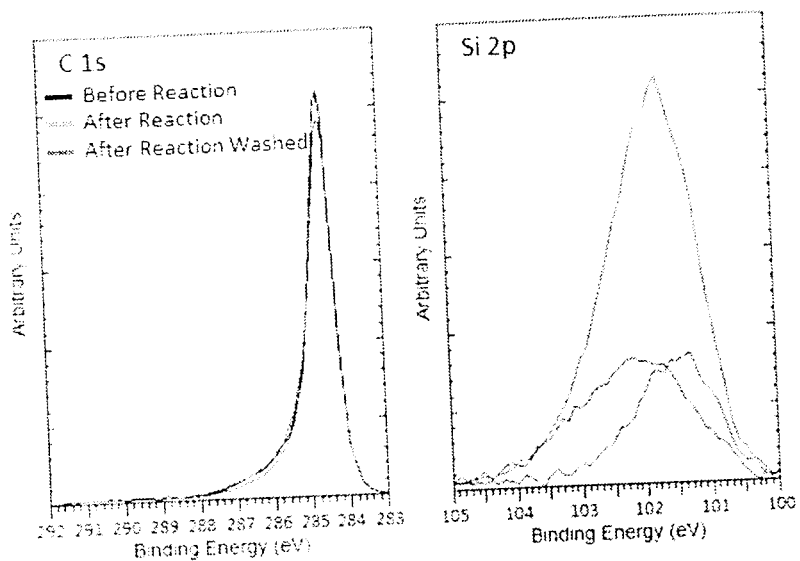
Figure 16A
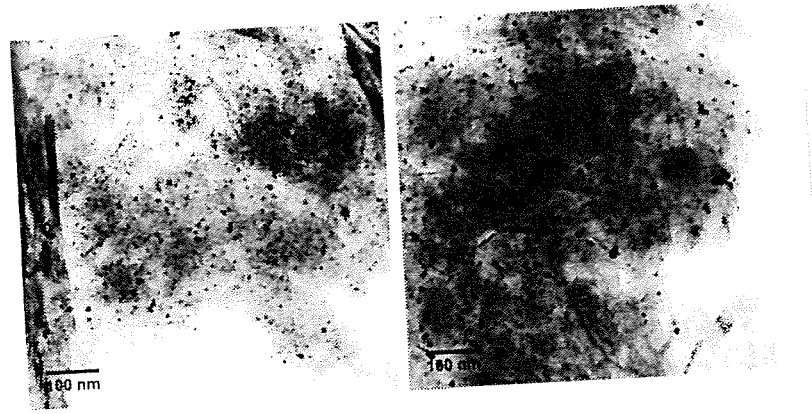
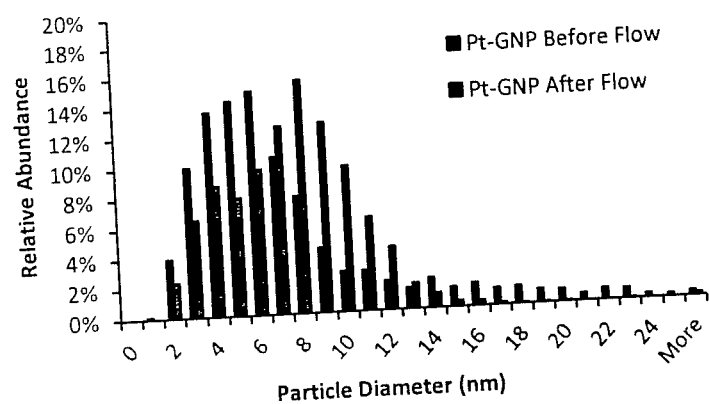
Figure 16B

CARBON BASED MATERIALS AS SOLID-STATE LIGANDS FOR METAL NANOPARTICLE CATALYSTS

STATEMENT OF FEDERALLY SPONSORED RESEARCH AND DEVELOPMENT

This invention was made government support under Grant Number 1464630 awarded by the National Science Foundation Industry (NSF). The government has certain rights in the invention.

BACKGROUND OF THE INVENTION

Field of the Invention

The invention generally relates to improved metal nanoparticle catalysts, and has particular application to palladium (Pd) and platinum (Pt) nanoparticle catalysts, as well as to other metal nanoparticle catalysts. In embodiments, the invention provides high activity catalysts comprising nanoparticulate Pd or Pt supported on carbon based materials such as graphene, and methods of making the catalysts via, for example, strong electrostatic adsorption (SEA) of Pd or Pt precursors onto the carbon based materials, followed by solventless or low-solvent microwave irradiation. The processes are also applicable to other metal nanoparticle catalysts.

Description of Related Art

Palladium catalysts are highly sought after for the production of various materials in the pharmaceutical industry [1]. Suzuki, Sonagashira, and Heck chemical transformations are among the most extensively researched and utilized reactions [2-6]. The use of homogenous palladium catalysis for these reactions is not favored due to difficulties separating and recovering palladium from products [7-8]. Current research on palladium catalysts has shifted to the use of heterogeneous palladium catalysis in attempts to prevent palladium from contaminating the desired product [9]. Heterogeneous catalysis relies on supporting palladium or other metals on supports that are more easily separated from the product due to the large size of the support. A palladium supported catalyst that is highly active, recyclable, easily separated, and is stable with regards to palladium leaching is highly desired [8, 10,11]. To achieve these benefits, the heterogeneous palladium catalyst must be synthesized in such a way as to provide excellent metal distribution with respect to palladium size and loading, and on a support capable of strongly anchoring palladium.

Strong electrostatic adsorption (SEA) is one synthetic method that has been used for high quality solid supported metal catalyst preparation including Pd, Cu, Co, Ru, Ni, and Pt on silica [12], Pt on carbon xerogel [13], and Pt on activated carbon, carbon black and graphitic carbon [14, 15]. This straightforward and rational method has been proven to produce highly dispersed metals on various supports. The SEA method calls for precise control of the pH of the precursor solution relative to the point of zero charge (PZC) of the support to maximize electrostatic interaction between the charged surface groups (typically hydroxyl groups) and oppositely charged metal coordination complex [16]. This process results in a strongly adsorbed monolayer of metal complex that is then reduced in the presence of hydrogen to form small metal nanoparticles and retain excellent metal dispersion [15].

The support material for a solid supported catalyst is often chosen based on the ability to anchor palladium, and cost. Graphene materials have recently been shown through computational and experimental work to provide a significantly higher binding energy for palladium and act as a charge reservoir that can enhance the catalytic activity of palladium for Suzuki reactions [17]. The binding energies of palladium clusters to the carbon atoms at defect sites are higher than non-defected basal plane carbon [17]. Additionally, oxygen groups and defect sites of graphene facilitate higher adsorption of palladium [17,18]. Synthesizing small Pd clusters or nanoparticles in defect sites of graphene supports which facilitate increased catalytic activity and stronger anchoring of metal catalysts is of paramount importance. However, cost and production scalability issues of pristine graphene are the most significant inhibitors of use of graphene in many applications including catalysis. Graphene oxide (GO) and reduced graphene oxide (rGO) are commonly utilized alternatives that can be produced in larger quantities with less difficulty and in a more cost-effective manner [16,19-20]. Furthermore, GO and rGO contain defects and oxygen containing functional groups that can strengthen and increase palladium graphene interaction [16,21]. Another alternative to pristine graphene is graphene nanoplatelet aggregates (GN). This relatively new material is significantly more cost effective, less than $1/g, and easily produced in greater quantities than pristine graphene, GO, and rGO.

Voiry et al. utilized an efficient and quick microwave treatment method to completely exfoliate GO, and remove oxygen content which resulted in a reordering of basal plane carbon [22]. The resulting microwave reduced material is more similar to pristine graphene than previous chemical reduction methods, although some defect sites were found depending on how the basal plane reordered. The researchers proposed the high order of graphene is due to some reordering of the carbon structure occurring at the extremely high temperatures reached during microwave treatment [22]. Thus, microwave treatment of defected graphene like materials can be used to improve the properties closer to that of pristine single layer graphene.

Kumar et al. have demonstrated a multi-step microwave irradiation method to engineer nanoholes in GO with relatively large palladium nanoparticles [23]. The research used ion exchange to obtain palladium acetate on the surface of GO followed by a multi-step low (700 W) and high power (900 W) microwave irradiation to form relatively large palladium nanoparticles and nanoholes.

There is a need in the art to provide improved, straightforward, high throughput methods to produce inexpensive Pd catalysts on graphene or graphene-like supports with high catalytic activity.

SUMMARY OF THE INVENTION

Other features and advantages of the present invention will be set forth in the description of invention that follows, and in part will be apparent from the description or may be learned by practice of the invention. The invention will be realized and attained by the compositions and methods particularly pointed out in the written description and claims hereof.

Carbon based materials as catalyst supports have shown tremendous promise for improving catalytic activity. In particular, Pd nanoparticles supported by graphene defects have been shown to improve catalytic activity in Suzuki reactions, but understanding their formation and factors that affect their formation is still elusive. As one example, a new synthetic method has been developed which combines i) a strong electrostatic adsorption (SEA) method for directed ionic Pd precursor uptake and, as a key feature, ii) a new solventless microwave irradiation method to simultaneously form Pd nanoparticles and graphene defect sites or holes. The resulting Pd-defect interactions provide more strongly anchored metal nanoparticles and lowered activation energy for catalytic reactions. Catalytic activities an order of magnitude higher than commercial Pd-carbon catalysts were obtained using this new method with low microwave powers, short reaction times, under atmospheric conditions, and without the use of reducing agents or solvents. The systematic comparison of catalysts synthesized from four different graphene materials and two different Pd precursors revealed Pd-graphene defects form through three routes that are affected by the initial oxygen content of the graphene support and the choice of ionic Pd precursor. The invention thus provides improved ways to produce inexpensive and high throughput Pd on carbon-based supports with the requisite characteristics for high catalytic activity, and has application to the formation of other metal nanoparticle catalysts such as Pt catalysts, for which similar results have been obtained.

In particular, a highly active graphene-supported platinum nanoparticle catalysts have been synthesized using strong electrostatic adsorption with solventless microwave adsorption (SEA-MW) as described herein. The Pt catalyst is useful for, for example, solventless hydrosilylation reactions of a variety of olefins. The catalyst has demonstrated exceptional catalytic activity and stability for hydrosilylation reactions (turnover frequency "TOF"~$10^5$ hr−1, turnover number "TON"=$7.8 \times 10^5$) at relatively mild conditions (mild temperature, ambient pressure, and without the need for an inert atmosphere). The catalyst also exhibited functional group tolerance over a broad range of industrially relevant substrates with minimal metal leaching. In addition, the Pt catalyst system was successfully translated into a packed bed platform and used to carry out continuous hydrosilylations reactions. This heterogeneous catalyst thus exhibits high activity, great recyclability, excellent functional group tolerance, and the ability to be used in continuous flow reactions to provide significant advantages over traditional commercial homogeneous Pt catalysts.

The disclosure provides a method of hydrosilylating an alkene, comprising providing a Pt catalyst, wherein the Pt catalyst is made by a method comprising i) depositing a Pt precursor on a carbon-based material; and ii) irradiating carbon-based material comprising deposited Pt precursor with radiant energy sufficient to attach Pt from the Pt precursor to the carbon-based material, thereby forming a Pt catalyst; and contacting the alkene with the Pt catalyst in the presence of a hydrosilylating agent. In some aspects, the carbon-based material is a graphitic material. In some aspects, the graphitic material is a graphene-based material. In other aspects, the graphene-based material comprises one or more of GP1-5, graphene oxide (GO), reduced graphene oxide (rGO), graphene nanoplatelets (GN), graphene nanoplatelet aggregates, graphene nanotubes, monolayer graphene, few-layer graphene (FLG) and multilayer graphene (MLG). In further aspects, the step of depositing is performed by loading the graphene-based material with the Pt precursor via strong electrostatic adsorption (SEA), wherein the loading takes place in an aqueous solution. In additional aspects, prior to the step of irradiating, the method further comprises the steps of: separating graphene-based material loaded with Pt precursor from the aqueous solution; and drying the graphene-based material loaded with Pt precursor. In yet further aspects, the method further comprises, prior to the step of loading, the steps of determining an optimum pH for SEA of the Pt precursor to the graphene-based material and adjusting the pH of the aqueous solution to the optimum pH. Further aspects includes those wherein the step of depositing is performed by dry impregnation, charge enhanced dry impregnation, wet impregnation, precipitation, co-precipitation, precipitation-impregnation or deposition precipitation. In some aspects, the radiant energy is microwave energy. In other aspects, the graphene-based material is GN. In further aspects, the Pt precursor is $PtCl_4^{2-}$. In additional aspects, the step of irradiating is performed at a fixed temperature. In yet additional aspects, the fixed temperature is 160° C. In some asepcts, the alkene is 1-octene. In further aspects, the hydrosilylating agent is $(Me_3SiO)_2MeSiH$. In other aspects, the Pt catalyst comprises Pt nanoparticles that are 10 nm or less in size.

BRIEF DESCRIPTION OF THE DRAWINGS

FIGS. 6A and B. High Resolution Transmission Electron Microscope images and histograms of A) Pd-GP_A and B) Pd-GP_B SEA-MW catalysts.

FIGS. 8A and B. High Resolution Transmission Electron Microscope images and histograms of A) Pd-rGO_A and B) Pd-rGO_B SEA-MW catalysts.

FIGS. 13A and B. Calculated TOF based on A) total Pd mol % and B) active Pd sites mol %. Commercial 10 wt % Pd on activated carbon (black), commercial 10 wt % on activated charcoal (white), graphene supported catalysts from PdCl$_4^{2-}$ (dark gray), and graphene supported catalysts from Pd(NH$_3$)$_4^{2+}$ (light gray).

FIGS. 16A and B. A, High resolution x-ray photoelectron spectroscopy with content quantitative scale of silicon 2p relative to carbon 1s spectra. B, TEM images before (left) and after (right) packed bed reactor experiment and corresponding histogram of Pt-GNP particle size before and after experiment.

DETAILED DESCRIPTION

Figure 1A:
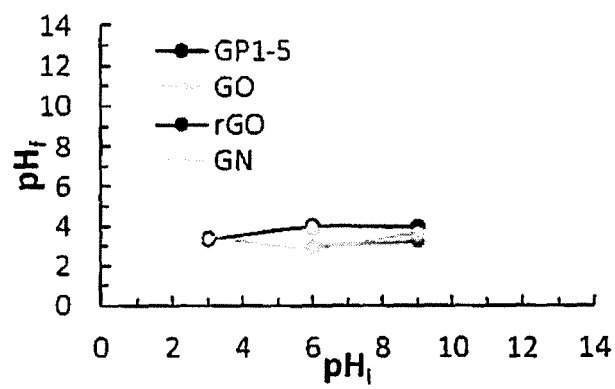
FIGS. 1A and B. A, Point of zero charge measurements for graphene samples: GP1-5, GO, and rGO and GN, are measured at 3 initial and final pH values; B, pH shift measurements for various graphene samples: GP1-5, GO, rGO and GN.

The invention provides methods of producing metal nanoparticle catalysts, such as Pd or Pt catalysts, by, for example, 1) depositing the metal onto a carbon-based material, thereby forming an intermediate carbon-based material with metal deposited thereon; and then 2) irradiating the intermediate material with radiant energy, such as microwave energy. The carbon-based material may be graphitic or non-graphitic in nature. In some aspects, intermediate material is dry when the step of irradiating is performed. However, this is not always the case. In some aspects, the intermediate material may be in solution (but generally without a reducing agent), or may be associated with a minimal amount of a solvent when the intermediate material is formed by a technique which may be but not limited to wet impregnation, precipitation, deposition precipitation, co-precipitation, precipitation-impregnation, dry impregnation, incipient wetness impregnation, or charge enhanced dry impregnation, when deposition of the metal occurs.

In some exemplary aspects, the methods involve the use of strong electrostatic adsorption (SEA) of metal precursors, such as Pd or Pt precursors, onto graphene based materials followed by solventless microwave irradiation, resulting in the simultaneous formation of, for example, Pd or Pt nanoparticle catalysts supported on i) the surface of the graphene based materials and ii) in/on/within defects/holes in the graphene based materials. It is noted that in the case of non-graphitic supports, the support material can undergo carbon rearrangement during irradiation and thereafter exhibit graphitic carbon properties.

Definitions:

"Dry impregnation" (also called incipient wetness impregnation (IW or IWI), capillary impregnation, or pore filling, or) is a technique for the synthesis of heterogeneous catalysts. Typically, an active metal precursor is dissolved in an aqueous or organic solution and the metal-containing solution is added to a catalyst support containing the same pore volume as the volume of the solution that is added. Capillary action draws the solution into the pores. Solution added in excess of the support pore volume causes the solution transport to change from a capillary action process to a diffusion process, which is much slower. The catalyst can then be dried and calcined to drive off the volatile components within the solution, depositing the metal on the catalyst surface. The maximum loading is limited only by the solubility of the precursor in the solution. The concentration profile of the impregnated compound depends on the mass transfer conditions within the pores during impregnation and drying.

"Charge enhanced dry impregnation" refers to conducting dry impregnation after inducing strong electrostatic interactions between the dissolved metal precursor and the support. This is generally done by acidifying or basifying the impregnating solution to the extent needed to charge up the surface of the metal precursor.

A "carbon-based material" refers to all varieties of substances composed solely or principally (e.g. at least 50, 60, 70, 80 or 90%) of the element carbon.

The carbon-based material may be "graphitic" or "non-graphitic". "Graphitic carbon" refers to all varieties of carbon-based material in the allotropic form of graphite irrespective of the presence of structural defects. The use of the term "graphitic carbon" is justified if three-dimensional hexagonal crystalline long-range order can be detected in the material by diffraction methods, independent of the volume fraction and the homogeneity of distribution of such crystalline domains. Otherwise, the term "non-graphitic carbon" should be used. Graphene is a form of graphitic carbon. In particular, graphene is a single layer or two-dimensional sheet of long-range order hexagonally arranged carbon atoms.

Thus, "non-graphitic carbon" refers to carbon-based material in which three-dimensional hexagonal crystalline long-range order cannot be detected by diffraction methods.

"Carbon allotropes" refers to the several different crystalline forms of carbon, examples of which include but are not limited to: nanotubes, nanofibers, nanoribbons, nanorods, fullerenes (e.g. buckyballs), etc.

"Low-solvent" conditions refers to conditions wherein the only solvent that is present during irradiation is that which is present in the void spaces between particles, such as occurs during dry impregnation.

By "Strong Electrostatic Adsorption" (SEA) as used herein refers to the precise control of the pH of the metal precursor solution relative to the point of zero charge (PZC) of the support to maximize electrostatic interaction between the charged surface groups (typically hydroxyl groups) and oppositely charged metal coordination complex. This process results in a strongly adsorbed monolayer of metal complex.

General Methods

In general, methods of making the metal catalysts disclosed herein include a step of depositing a metal precursor on a carbon-based support material. In order to do so, the metal precursor is combined with a suitable carbon-based support material under conditions and using techniques that permit or enhance the deposition or adsorption of the metal precursor onto the carbon-based support material. Examples of suitable techniques include but are not limited to: solution-based techniques using strong electrostatic adsorption (SEA), dry impregnation or incipient wetness impregnation, charge enhanced dry impregnation, precipitation, coprecipitation, deposition precipitation, precipitation-impregnation.

The carbon-based material on which the metal precursor is deposited may be graphitic or non-graphitic. Exemplary support materials include but are not limited to: graphitic carbon, carbon allotropes, single and multi-walled carbon nanotubes, carbon nanofibers, graphene and various forms of graphene, fullerenes (e.g. buckyballs) and amorphous carbon. Those of skill in the art will recognize that "amorphous carbon" encompasses many subtypes such as carbon black, activated carbon, charcoal, activated charcoal and others, all of which are encompassed herein.

In particular, "graphene-based support material" or "graphene-based support" or "graphene based-material" refers to any support material that is or is made from or comprises graphene, including natural and synthetic forms of graphene, and physically or chemically modified forms of graphene. Suitable graphene based materials include but are not limited to: graphene powder (e.g. graphene powder having 1 to 5 layers (GP1-5)), graphene oxide (GO), reduced graphene oxide (rGO), graphene nanoplatelets or graphene nanoplatelet aggregates (GN), graphene nanotubes, monolayer graphene, few-layer graphene (FLG, with e.g. 2-5 layers), or multilayer graphene (MLG, with e.g. 2-10 layers). In some aspects, the graphene based material is GN, because it is less expensive than alternative graphene based materials and yet the catalysts made therewith exhibit excellent catalytic capability/efficiency.

In some aspects, the carbon-based support material is amorphous (non-graphitic). Examples of suitable non-graphitic carbon that can be used include but are not limited to: activated carbon, activated charcoal, carbon black, charcoal, and other subcategories known in the art.

In some aspects, the starting material is a Pd or Pt starting material or precursor. However, the methods disclosed herein may also be used to make catalysts comprising other metals (e.g. Au, Ag, Pd, Co, Cu, Ni, Ir, Re, Os, Rh, Ru, Mo, W, Zr, Zn, Y, Fe, Mn, Cr, V, Ti, Sc, Ce, Pr, Nd, Sm, Gd, Hom, Er, Yb, Al, Ga, Sn, Pb, In, Mg, Ca, Sr, Na, K, Rb or Cs) and/or "mixed" catalysts comprising two or more types of metals (e.g. about 2, 3, 4, 5, 6, 7, 8, 9, or 10 types of metals). The precursor forms of the metals are those which are generally known, e.g. anionic or cationic salts such as Cl, Br, etc. or other anionic and cationic coordination complexes containing ligands and mixtures of ligands such as boride, iodide, cyanide, ethylene diamine, and ethylenediamminetetraactic acid (EDTA). However, for some techniques, e.g. impregnation techniques, charged precursors are not required and precursors comprising acetate, acetyl acetate, etc. may be used. In addition, a single type of metal may be used but a combination of more than one type of precursor may be used, e.g. the reactions may be performed using both $PdCl_4^{2-}$ and $Pd(NH_3)_4^{2+}$ in a signal reaction, as an example.

For Pd in particular, the Pd starting materials (precursors) may be anionic or cationic. Pd precursors that are used include but are not limited to: $PdCl_4^{2-}$, $Pd(NH_3)_4^{2+}$, and other anionic and cationic coordination complexes containing ligands and mixtures of ligands such as boride, iodide, cyanide, ethylene diamine, and ethylenediamminetetraactic acid (EDTA). However, for some techniques, e.g. impregnation techniques, charged precursors are not required and precursors such as Pd acetate, Pd acetyl acetate, etc. may be used.

For Pt in particular, the Pt starting materials (precursors) may be anionic or cationic. Pt precursors that are used include but are not limited to: $PtCl_4^{2-}$, $Pt(NH_3)_4^{2+}$, $Pt(NH_3)_2^{4+}$, and other anionic and cationic coordination complexes containing ligands and mixtures of ligands such as hydroxy, chloride, bromide, boride, iodide, cyanide, ethylene diamine, and ethylenediamminetetraactic acid (EDTA). However, for some techniques, e.g. impregnation techniques, charged precursors are not required and precursors such as Pt acetate, Pt acetylacetonate, Platinum disulfide, etc. may be used.

Combining the carbon-based support material and the metal precursor results in production of an intermediate material that is the support material plus metal precursor, e.g. adsorbed Pd or Pt precursor. In the intermediate material, the metal precursor may be held onto the support by electrostatic forces, or by, e.g. van der Waals forces, etc. The intermediate material may or may not be dried to remove solvent prior to conducting further method steps. For example, if a SEA method is used, a drying step may be used. However, if dry impregnation is used, a drying step may or may not be used.

Significantly, according to the methods, the metal precursor that is adsorbed (deposited, taken up/uptaken, loaded) onto the support is then attached (immobilized, anchored) to the support by irradiating the support-precursor with radiant energy. The radiant energy may be microwave energy. Without being bound by theory, it is believed that in the process of exposing the support and metal precursors to irradiation i) metal precursors are reduced to metal nanoparticles, ii) supports can undergo carbon rearrangement resulting in more ordered graphite or graphene, graphene defects, vacancies, or holes, and iii) the resulting formed nanoparticles are strongly anchored, immobilized, or bound to the surface/defects/vacancies/holes of the support. It is believed that, without being bound by theory, the support acts as a solid state ligand to strongly anchor or immobilize the metal nanoparticles in/on/within defects/holes or surface of the support. In some cases, a carbon metal alloy (e.g. PdC) can form through the irradiation process which offers another type of binding/anchoring of metal to the support. The microwave irradiation facilitates relatively strong binding energies to anchor or immobilize the nanoparticles to the surface of the support.

The following section generally describes examples of methods in which graphene-based materials are used to make Pd or Pt catalysts via SEA. However, the descriptions in this section are generally applicable to methods which use other support materials and methods, e.g. pH conditions for desired or optimal metal uptake, the amount of graphene based support, level of metal loading of the support, the desired levels of activity of the catalyst, drying methods and conditions, and the step of exposure to radiant energy (including the power levels, time. etc.), are generally the same for non-graphene based materials and non-SEA techniques, and for other types of metal precursors.

Exemplary Graphene-Based Methods

When the carbon-based material is graphene-based, in some aspects, the first step of the method involves combining an ionic (charged) Pd or Pt precursor and the graphene-based material in liquid solution. The pH of the solution is then titrated to ensure that the charge of the Pd or Pt precursor is suitable or optimized for electrostatic adherence to the graphene-based material that is being used. As a result, a relatively uniform layer of the metal precursor is formed on the exterior surfaces of the graphene based material, i.e. the exterior surfaces comprise a high local concentration of Pd or Pt precursor adsorbed thereto via electrostatic forces, the basis of SEA. The liquid is removed and the graphene based material with the adsorbed Pd or Pt is dried. The dried material is then exposed to microwave irradiation (generally low levels of microwave irradiation) for a short period of time (e.g. minutes). Nevertheless, this time period is sufficient to permit the development of defects (holes) in the surface of the graphene based material by the microwaves and in some cases, facilitated by heating of the attached Pd or Pt, which pyrolyzes the graphene. In addition, the application of microwave irradiation secures the Pd or Pt species onto the surface of the graphene based material, with at least a portion of the Pd or Pt species being secured in the holes in the graphene based material. The resulting Pd or Pt nanoparticles catalysts are strongly supported on the graphene based material and in the defects/holes of the graphene based support material. The nanoparticles are advantageously very small e.g. less than 10 nm, and their concentration (density) is high. The resulting catalysts exhibit excellent catalytic performance, compared to prior art Pd and Pt catalysts.

Without being bound by theory, it is believed that metal precursor binds to the graphene by one or more, or all, of three possible mechanisms: 1) The metal precursor electrostatically adsorbs to preexisting defects in the graphene support even prior to microwave irradiation, e.g. vacancy-defect sites, Stone-Wales defect sites, oxygen functional group defect sites, etc. 2) By controlling the pH through titration, oxygen functional groups present in/on the graphene support are protonated or deprotonated and rendered more likely to electrostatically adsorb an anionic or cationic metal precursor, respectively. Upon microwave irradiation, the oxygen functional groups are removed, forming a defect site, and available metal precursor localizes in or on the defect site, effectively preventing carbon rearrangement to a more ordered basal plane of carbon. 3) For anionic metal precursors, microwave irradiation of the metal precursor electrostatically adsorbed on protonated pi bonds of aromatic rings within the basal plane of graphene results in formation of metallic nanoparticles reaching exceptionally high temperatures that pyrolyze graphene, creating, e.g. Pd- or Pt-defect sites.

One of the key improvements or benefits is that this catalyst can be made under ambient environmental conditions (e.g. air) and can be stored under ambient environmental conditions (e.g. stored in vial that can be open to air on a benchtop/shelf) without any loss of catalytic activity for over at least a year. Many metal based catalysts must be stored under inert environments (e.g. nitrogen or argon) or stored in a glove box which can be expensive, time consuming, or complicated.

Initially, pH conditions for maximum metal uptake/deposition onto the support are determined using the SEA method. Based on SEA calculations, it is possible to precisely control the pH of solutions comprising, e.g. a Pd or Pt precursor relative to the point of zero charge (PZC) of the support in order to maximize electrostatic interaction between the charged or especially the polar surface groups of the support (e.g. OH, O$^-$, OH$_2^+$, protonated pi-bonds) and the oppositely charged Pd or Pt metal coordination complex. The objective is to ensure that the charge of the metal precursor is suitable or optimized for optimal electrostatic adherence to the graphene based material. Basically, if the metallic precursor is positively charged it is advantageous for e.g. OH groups to be deprotonated to foster adherence of the precursor, and if the metallic precursor is negatively charged it is advantageous for e.g. OH groups and/or pi bonds of basal plane carbon of graphene to be protonated to foster adherence of the precursor.

The PZC of a graphene-based support is determined e.g. by either measuring the pH of the incipiently wet sample of graphene or measuring the isoelectric point (isoelectric point is synonymous with point of zero charge for this application) zeta-potential using dynamic light scattering of the graphene in aqueous solution: An exemplary 3-point PZC measurement method is described in Park, et al. *Journal of Colloid and Interface Science* 1995, 175, 239-252 (reference 25 herein). Briefly, initial pH solutions of 3.0, 6.0, and 9.0 were added in small increments until incipient wetness is obtained and then a pH probe is used to measure the PZC. When the pore volume of the graphene matches the volume of the solution, it is no longer a powder but is a "solid ball" that is neither a powder or fully wet. At pH values above the PZC, the graphene-based support is overall negatively charged and at pH values below the PZC, the graphene-based support is overall positively charged.

In addition, for each support, a pH shift experiment may be conducted to account for pH changes resulting from support addition to an aqueous solution (the final reaction with the metal precursor is conducted in an aqueous solution). As an example, a suitable quantity of a support is placed in each of multiple (e.g. 6-20, such as 12) aqueous liquid samples (e.g. nanopure or deionized water) at several different initial pH (pHi) values and allowed to equilibrate with thorough mixing (e.g. with shaking). The pHi's may be adjusted using e.g. HCl, NH$_4$OH, etc. After thorough mixing, the final pH (pHf) of each sample is measured and the change in pH is used as a guide for palladium uptake experiments. In addition, for each support, a pH shift experiment is conducted to account for pH changes resulting from support addition to an aqueous solution (the final reaction with the metal precursor is conducted in an aqueous solution). Some supports at certain high concentrations (high surface loading) can significantly alter the pHi→pHf. Therefore a pH shift experiment allows one to account for the support change on pH and obtain a useful range of pHf when a precursor aqueous solution (e.g. Pd or Pt) is used. This is done to conserve expensive precursors such as Pd.

The pH conditions for desired or optimal metal uptake are established for a particular graphene based support and a particular metal precursor which is to be loaded onto the support. Dried graphene-based support is added to a solution of the precursor at several pH values (e.g. in nanopure or deionized water). Nanopure water is, for example, deionized water that is also filtered in several ways to remove any contaminants not removed in the deionizing steps. The pH values are selected using the pHf values obtained in a previous pH shift experiment for the particular graphene based support. For example, the Pd precursor is present in the solutions at a concentration of about 10 to 10,000 ppm, e.g. about 50 to 100 ppm, such as about 100, 150, 200, 250, 300, 350, 400, 450 or 500 ppm or higher. The amount varies depending on the desired loading of Pd. Similar values apply to Pt and other metals. Some graphene supports can accommodate higher concentrations of metal. Those of skill in the art will recognize that the concentration that is used depends on how much loading is desired and the type of support, and can be determined by routine optimization. For example, 5% loading may require only 100 ppm whereas 50% loading may require 1000 ppm. In addition, higher concentrations of support may require even higher amounts such as 3000 ppm or more.

The amount of graphene based support is based on a surface loading (surface area of graphene to volume ($m^2$/L) of metal solution (such as a Pd or Pt solution), and is about 100 to 3,000, e.g. about 100, 500, 1000, 1500, 2000, 2500 or 3000 $m^2$/L, and is typically e.g. about 500 or 1500 $m^2$/L. The final volume of the solutions may be any that is convenient to work with, e.g. 25-4,000 ml and is limited only by the size of the container and other available equipment. The solutions are then left to allow adsorption of the metal to the support, for example, with shaking for e.g. 10 minutes to 2 hours, such as 30-90 minutes or more (for example, one hour). The temperature may range from e.g. about 0° C. to about 90° C., and may be room temperature. Initial and final aliquots of each sample are obtained and the metal loading or uptake is measured. For example, aliquots may be filtered to remove graphene based support, and residual metal in the solution is measured, for example, using inductively coupled plasma optical emission spectroscopy (ICP-OES). Metal uptake is calculated by determining the difference between initial and final metal concentrations in the solutions, and dividing that value by the graphene based support surface loading used and the MW of the metal.

The pH that results in maximal metal loading of the support is generally is selected for further catalyst production, e.g. for scale-up. Exemplary desirable loading values (e.g. for a monolayer Pd precursor uptake) include but are not limited to e.g. about 0.1 to about 1.5, e.g. about 0.1, 0.2, 0.3, 0.4, 0.5, 0.6, 0.7, 0.8, 0.9, 1.0, 1.1, 1.2, 1.3, 1.4, or 1.5, including all 0.01 decimals in between each value, e.g. 0.11, 0.12, 0.13, etc. up to about 1.5, the units being µmol Pd/$m^2$ of support surface area. However, some supports may exhibit even higher loading. Alternatively, metal loading can be reported as weight percent, which is e.g. the g of Pd per g of graphene support and Pd. For non-monolayer Pd precursor uptake, e.g. generally for non-SEA techniques, the loading values may be higher.

Importantly, the present methods allow the production of metal catalysts, e.g., Pd or Pt catalysts, having varying desired levels of activity, i.e. the level of density of metal that is deposited is controllable. Generally, the desired activity is as high as possible but that may not always be the case. By calibrating/monitoring the amount of metal that is deposited on the graphene based support, e.g. by varying the extent of titration, the metal precursor and the support that is used, and/or the power of the microwave radiation and the time of exposure to the radiation, the activity of the final product can be modulated or tuned. In addition, by using the same starting materials and keeping the reaction conditions constant or reproducible from batch to batch, the level of activity of the catalysts can be kept the same from preparation to preparation, i.e. variability between batches is reduced.

Once the pH conditions for optimal or desired metal loading of a graphene based support have been determined, larger volumes of metal loaded support can be produced for conversion to a catalyst.

The metal (e.g. Pd, Pt, etc.) loaded support is removed from the solution by any suitable means or combinations thereof, e.g. centrifugation, washing, filtration, decanting, etc., and the loaded support is dried thoroughly. Drying (dessicating, dehydrating, etc.) is performed by any known method, e.g. by exposure to air, heating (e.g. drying oven), drying (e.g. under $N_2$, Ar, $H_2$/Ar gas), drying under vacuum, etc. The result is generally a dried powder.

Following drying, the dried loaded support is ready for conversion to a catalyst. Accordingly, the metal loaded support is exposed to radiant energy, in particular, to a relatively low level of microwave irradiation. However, other forms of radiant energy may also be used, e.g. ultraviolet (UV), broad spectrum light, etc. Significantly, irradiation is performed in a solventless manner and without reducing reagents, i.e. the dried material is directly subjected to irradiation without being suspended in or mixed with a solvent. In some aspect, the methods described herein are carried out at fixed low microwave powers for short reaction times. "Low microwave powers" refers to microwave powers in the range of from about 5-500 Watts, e.g. about 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195 or 200 W or higher, e.g. about 250, 300, 350 400, 450 or 500 W, and in the preferred ranges of from about 100 to about 200 W, or about 200-300 W. "High microwave powers" may also be used and refer to microwave powers above 500 W, such as 600, 700, 800, 900 or 1000 W, or even much higher, e.g. some industrial microwaves going up to powers of 100,000 W, so that powers such as 5,000-10,000 W or even more may be used. Those of skill in the art are aware of how one would optimize the power level and timing of the reaction in order to achieve a desired level of metal attachment to the support. In some aspects, the microwave power is 200 W. In addition, alternating patterns of irradiation may be used by e.g. irradiating at a first power level for 1-2 seconds, then a second power level for 5 seconds, then the first power level or a third power level for 1-2 seconds, etc. A very large number of different combinations of times and power levels can be conceived, and all are intended to be encompassed by the present disclosure.

Alternatively, the reactions may be performed at a particular (fixed) temperature in the range of from, e.g. about 100 to about 300° C., e.g. about 100, 110, 120, 130, 140, 150, 160, 170, 180, 190, 200, 210, 220, 230, 240, 250, 260, 270, 280, 290, or 300° C. or more. For example, some catalysts are manufactured using high temperatures in the range of from about 300 to about 2000° C., e.g. about 300, 400, 500, 600, 700, 800, 900, 1000, 1100, 1200, 1300, 1400, 1500, 1600, 1700, 1800, 1900, or 2000° C., depending on the starting materials and the desired outcome, and those ranges may be employed in some aspects of the present methods. Those of skill in the art will recognize that irradiation (e.g. microwave) can result in local superheating to these high temperatures or even greater. It is well within the purview of those of skill in the art to optimize reactions conditions without undue experimentation.

It is noted that when performing fixed temperature microwave heating, the corresponding microwave powers, relative to temperatures below 300° C., are typically lower than 100-150 W. It is further noted that the power may "spike" to around 100-150 W for 4 seconds depending on the graphene support and then will maintain temperature with e.g. <25 W power "spikes". For example, for Pt catalysts made with $PtCl_4^{2-}$, a microwave reduction temperature of 160° C. for 10 minutes was selected. To reach and maintain a temperature of 160° C., an initial spike of microwave power of approximately 100 W for 4 seconds followed by intermittent power spikes <25 W was used.

While a conventional microwave may be used, the present methods are well-suited to being carried out using industrial high throughput microwave generators, e.g. continuous microwave systems, batch microwave systems, various industrial microwave generators, belt driven flow microwave technology, etc.

When an SEA method/technique is used, the resulting dried powder (support with loaded metal precursor) is generally exposed to radiant energy (e.g. microwave energy) for a relatively short reaction time. A "short reaction time" refers to a reaction time in the range of from about 1 second to about 30 min, depending on the desired properties of the catalysts, e.g. in the range of from about 1-60 seconds (such as above 1, 5, 10, 15, 20, 25, 30, 35, 40, 45, 50, 55 or 60 seconds), or about 1 to 30 min such as 1, 5, 10, 15, 20, 25 or 30 min. For fixed temperature microwave parameters the time may be, for example, about 1-10 minutes, and for fixed microwave power parameters, the time may be about 1-15 seconds (e.g. 1, 2, 3, 4, 5, 6, 7, 8, 9, 10, 11, 12, 13, 14 or 15 seconds). The exposure may be constant or intermittent, and the sample that is irradiated may be moved during exposure, e.g. rotated, spun, shaken, etc.

Generally, irradiation is conducted at atmospheric (ambient) pressure and environment, although in some cases, pressure may be applied or inert atmosphere can be used (e.g. nitrogen or argon). The reactions can be conducted under $H_2$. The pressures listed, for example, in Table 4 are the result of the microwave heating creating pressure in the vial. Those samples were not pressurized prior to heating.

Overall, reaction conditions are selected so as to rapidly form the catalyst, but also to limit the amount of nanoparticle growth and retain a uniform size distribution (very small particles and tight size distribution are preferred) while still facilitating the simultaneous formation of defect sites in graphene (e.g. Pd binds strongly to defect sites and is more active when supported by graphene defect sites, compared to support on the surface of graphene).

Catalysts

Regardless of the starting materials that are used, the resulting metal nanoparticles catalysts comprise ultrasmall metal clusters and nanoparticles immobilized in and on graphene-based support defect/hole locations. For example, the size of individual Pd clusters/nanoparticles is in the range of from about 0.5 to about 50 nm or greater, e.g. about 0.5, 1.0, 1.5, 2.0, 2.5, 3.0, 3.5, 4.0, 4.5, 5.0, 10, 15, 20, 24, 30, 35, 40, 45, 46, 47, 48 or 49 nm. For most supports the majority of nanoparticles are of the size about 0.5-10 nm, e.g. about 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5 or 10.0. In some aspects, the "size" refers to the average size of the metal particles. In other aspects, the "size" refers to the size of the smallest metal particles that are present, e.g. other larger metal particles may also be present on the support, but the presence of the "ultra-small" particles (e.g. less than about 10 nm) over about 5, 10, 20, 25, 30, 35, 40, 45, 50, 55, 60, 65, 70, 75, 80, 85, 90, 95% or more of the surface area of the support material, results in very high levels of catalytic activity, even if larger particles are present. Single metal atoms may also be present.

Generally, the Pd catalysts described herein have a Pd weight % loading of from about 1 to about 15 for graphene-bases supports, e.g. about 1, 2, 3, 4, 5, 6, 7, 8, 9, 10, 11, 12, 13, 14, or 15%. In some aspects, the Pd weight % loading is from about 1-5%, e.g. 1.0, 1.5, 2.0, 2.5, 3.0, 3.5, 4.0, 4.5 or 5.0%. However, other supports may accommodate up to e.g. about 70% (such as about 20, 30, 40, 50, 60 or 70%).

The activity of Pd catalysts made as described herein is very high, exhibiting turnover frequencies (TOFs, i.e. turnover per unit time) generally in the range of from about 1 to $10 \times 10^6$ $hr^{-1}$, e.g. at least about 1, 2, 3, 4, 5, 6, 7, 8, 9 or $10 \times 10^6$ $hr^{-1}$, for example, for a reaction such as a Suzuki reaction. For hydrosilylation reactions, a exemplary Pt catalyst TOF was about $1 \times 10^5$, and a turnover number "TON" was about $7.8 \times 10^5$, even at relatively mild conditions of temperature and at ambient pressure, without the using an inert atmosphere.

The metal catalysts made as described herein are advantageously recyclable in that they may be used repeatedly without a loss (or with only a minimal loss) of catalytic potency. That is, one reaction may be performed, the catalysts can be "washed" or rinsed to remove residual reactants, and the catalysts can then be reused to catalyze the same reaction again, or to catalyze an entirely different reaction. For example, the catalysts can generally be used e.g. from about 2-10 multiple times, such as 2, 3, 4, 5, 6, 7, 8, 9, 10, or more times (e.g. 20-30 times), without losing more than e.g. about 50% of their activity or less, e.g. 50, 45, 40, 35, 30, 25, 20, 15, 10, 5, or even 0% of the activity is lost after each use.

The methods of making a metal catalyst disclosed herein may be adjusted so as to scale the process as needed. The reactions may be carried out "at the bench" on a relatively small scale or may be readily scaled up to a level that is suitable for industrial manufacturing. For example, industrial microwave sources may be employed for the final reaction step, such as continuous microwave systems, batch microwave systems, various industrial microwave generators, purpose built microwave systems, etc. to achieve high throughput manufacturing of the catalysts.

Reactions and Products

Many reactions can be catalyzed by the catalysts described herein.

As an example, the Pd catalysts disclosed herein may be used to catalyze a number of chemical reactions, including but not limited to: cross-coupling and C—H activation pharmaceutical reactions such as Suzuki, Heck, Negishi, Sonogashira, hydrogenation, homocoupling, and oxidation reactions.

As a further example, the Pt catalysts disclosed herein are used to catalyze a number of chemical reactions, including but not limited to: hydrosilylation reactions in batch and continuous packed bed reactors i.e. catalytic hydrosilylation: the addition of Si—H bonds across unsaturated bonds, such as the hydrosilylation alkenes and alkynes; oxidations of hydrocarbons as well as oxygen containing ketones and alcohols; hydrogenations of unsaturated C—C and C—O bonds; cross coupling; hydrometallations; and metallations of organic compounds that Pt(0) catalysts have been reported to mediate, etc.

A plethora of products may be made using the catalysts described herein, such as but not limited to functionalized aromatic alkynes, functionalized aromatic amines, functionalized aromatic nitro compounds, functionalized aromatic imines, functionalized aromatic benyzylic materials, functionalized aromatic alcohols, functionalized aromatic halogens, functionalized aromatic ethers, functionalized aromatic aryl alkynes, functionalized aromatic aryl ethers, functionalized aryl and alkyl alkynes, functionalized aryl and alkyl amines, functionalized aryl and alkyl nitro compounds, functionalized aryl and alkyl imines, functionalized aryl and alkyl benzylic materials, functionalized aryl and alkyl alcohols, functionalized aryl and alkyl halogens, functionalized aryl and alkyl ethers and functionalized silyl aryl and alkyl ethers and silylized olefins. Using the catalysts of the invention, these valuable products, including many drugs that are commonly used to treat chronic or life-threatening illnesses, may be made more rapidly and cost effectively than was possible using prior art catalysts. Thus, they could be more widely available.

Other Catalysts

Other catalysts can also be made using the methods described herein, e.g. via a strong electrostatic adsorption uptake step or other methods of metal uptake as described elsewhere herein, followed by irradiation, e.g. microwaves. This facilitates a rational, controllable, and uniform uptake of metal precursor onto the surface of a support, such as a GNP support. In some aspects, the starting material is a Pd or Pt starting material or precursor. However, the methods disclosed herein may also be used to make catalysts comprising other metals (e.g. Au, Ag, Pd, Co, Cu, Ni, Ir, Re, Os, Rh, Ru, Mo, W, Zr, Zn, Y, Fe, Mn, Cr, V, Ti, Sc, Ce, Pr, Nd, Sm, Gd, Horn Er, Yb, Al, Ga, Sn, Pb, In, Mg, Ca, Sr, Na, K, Rb or Cs) and/or "mixed" catalysts comprising two or more types of metals (e.g. about 2, 3, 4, 5, 6, 7, 8, 9, or 10 types of metals).

It is to be understood that this invention is not limited to particular embodiments described herein above and below, and as such may, of course, vary. It is also to be understood that the terminology used herein is for the purpose of describing particular embodiments only, and is not intended to be limiting.

Where a range of values is provided, it is understood that each intervening value between the upper and lower limit of that range (to a tenth of the unit of the lower limit) is included in the range and encompassed within the invention, unless the context or description clearly dictates otherwise. In addition, smaller ranges between any two values in the range are encompassed, unless the context or description clearly indicates otherwise.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

EXAMPLES

Example 1

Electrostatic Adsorption-Microwave Synthesis of Palladium Nanoparticles on Graphene for Improved Cross-Coupling Activity 1 Introduction A combined SEA and solventless microwave reduction method (SEA-MW) was developed for four different types of commercially available graphene based supports and two different palladium precursors to better understand how to engineer Pd-defect interactions for increased catalytic activity. SEA with cationic and anionic precursors was used to specifically adsorb palladium on graphene based supports where defect sites could be engineered through microwave irradiation. The resulting catalysts were extensively characterized by powder x-ray diffraction (XRD), transmission electron microscopy (TEM), x-ray photoelectron spectroscopy (XPS), and chemisorption techniques. An initial Suzuki reaction was used to explicate the relationship between different ways in which Pd-defect interactions form and their effects on catalytic activity.

2 Experimental 2.1 Materials and Methods

Four commercially available graphene materials were selected: graphene powder 1-5 layers (GP1-5, Strem Chemicals), graphene oxide (GO, Strem Chemicals), reduced graphene oxide (rGO, Strem Chemicals), and graphene nanoplatelet aggregates (GN, Alfa Aesar). The as received materials properties were measured and are listed in Table 1. Dihydrogen tetrachloropalladate (II) ($H_2PdCl_4$) produced from palladium chloride ($PdCl_2$) in hydrochloric acid (HCl), and tetraamminepalladium(II) chloride monohydrate (Pd$(NH_3)_4Cl_2$) (Alfa Aesar, 99.9%) were selected as anionic and cationic palladium precursors respectively.

TABLE 1

Summary of commercially available graphene supports

| Graphene Name | Abbreviation | Approx. Cost | Surface Area B.E.T $(m^2/g)^a$ | Surface Area B.E.T $(m^2/g)^b$ | Micropore Percentage | Methylene Blue Surface Area (m2/g) | Total Pore Volume (mL/g) | $PZC^c$ |
|---|---|---|---|---|---|---|---|---|
| Graphene Powder (1-5 layers) | GP1-5 | $261/g | 650-750 | 589 | 20.1% | 662 | 39.6 | 3.75 |

TABLE 1-continued

Summary of commercially available graphene supports

| Graphene Name | Abbreviation | Approx. Cost | Surface Area B.E.T $(m^2/g)^a$ | Surface Area B.E.T $(m^2/g)^b$ | Micropore Percentage | Methylene Blue Surface Area (m2/g) | Total Pore Volume (mL/g) | PZC$^c$ |
|---|---|---|---|---|---|---|---|---|
| Graphene Oxide | GO | $180/g | 5-10 | — | — | 1744-2690 | 3.95 | 3.78 |
| reduced Graphene Oxide | rGO | $339/g | n.d. | 327 | 0.3% | 2254 | 1.37 | 2.96 |
| Graphene Nanoplatelet Aggresates | GN | <$1/g | 484.5 | 481 | 45.0% | 381 | 1.6 | 3.32 |

$^a$Measured by supplier
$^b$Surface area measured using BET analysis
$^c$Determined by pH shift at incipient wetness in accordance with [1]
$^d$PZC determined by measuring the isoelectric point using DLS zeta potential measurements at various pH values 2.2 Support Material Characterization
2.2.1 Surface Area and Microporosity Measurements Physisorption experiments were conducted for each support to measure the surface area and microporosity. All samples were also analyzed using a modified methylene blue (MB) method for determining surface area of supports in solution [24]. Briefly, a known amount of each support (4-20 mg) was suspended in a 40 mg/mL methylene blue solution and shaken for 1 hour, upon which an aliquot was centrifuged and the supernatant was analyzed by UV-VIS spectroscopy at 665 nm wavelength. The amount of methylene blue adsorbed was used to calculate the surface area using the relationship of 2.54 $m^2$/mg of MB adsorbed.

2.2.2 Point of Zero Charge and pH Shift Experiments

The PZC for each support material was measured using previously reported 3-point PZC measurement methods [25]. Briefly, initial pH solutions of 3.0, 6.0, and 9.0 were added in small increments until incipient wetness was obtained. Next, a pH probe was used to measure the PZC. The results are shown in FIG. 1A.

Figure 1B:
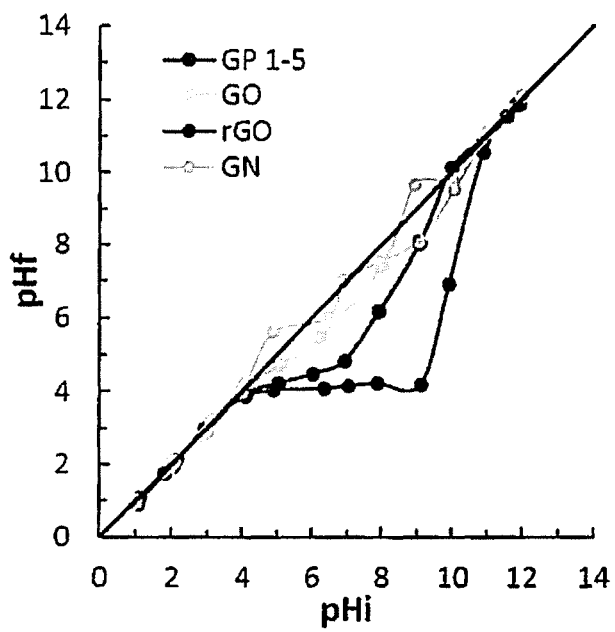
Figure 2:
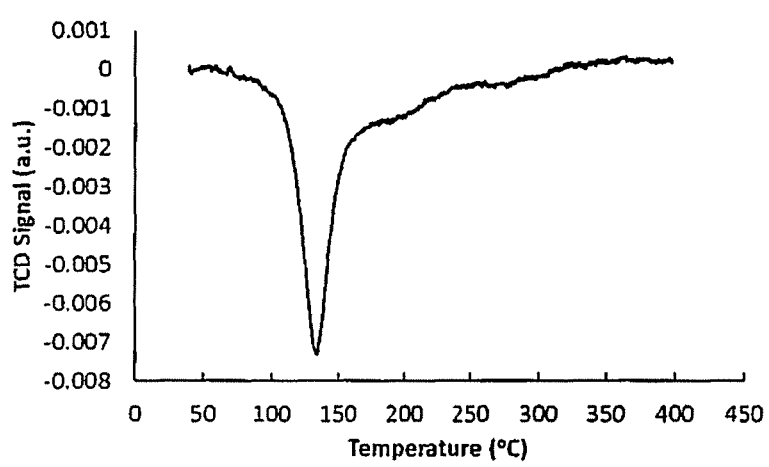
FIG. 2. Example of a Temperature Programmed Reduction (TPR) plot of temperature versus TCD signal detecting hydrogen loss indicating temperature at which reduction of sample is occurring for $Pd(NH_3)_4^{2+}$-GN.
Figure 3A:
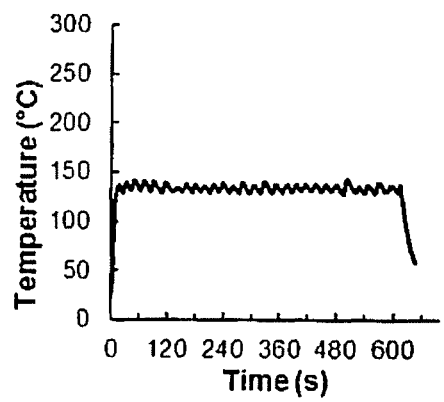
FIG. 3A-C. Example of solventless microwave reduction profile plots of A) temperature, B) power, and C) pressure versus time for $Pd(NH_3)_4^{2+}$-GN.
Figure 3B:
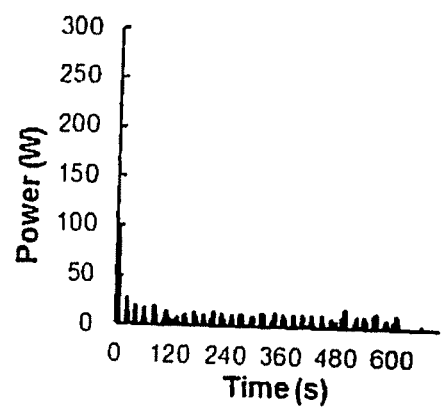
Figure 3C:
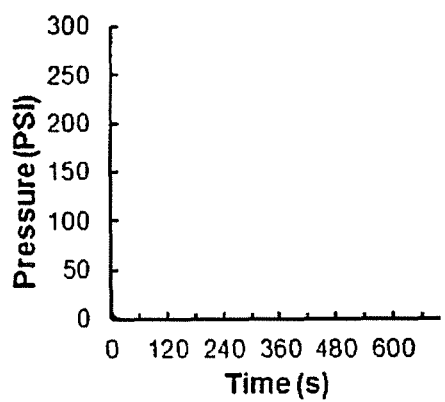
Figure 4A:
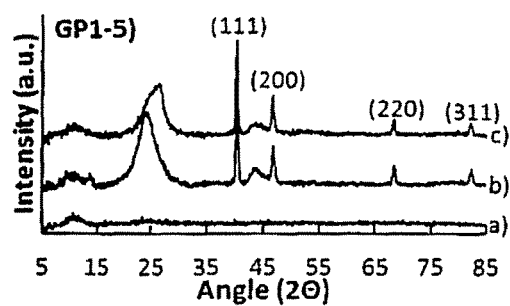
FIG. 4A-D. X-ray diffraction patterns for A, GP1-5; B, GO; C, rGO; and D, GN. a) support only, b) after $PdCl_4^{2-}$ SEA uptake, and c) after SEA-MW.
Figure 4B:
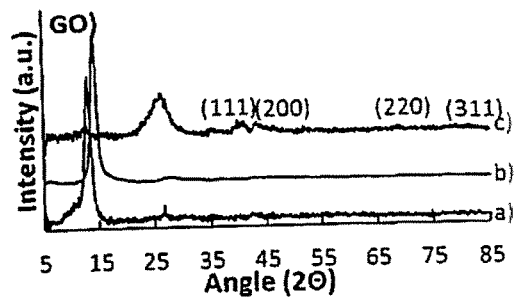
Figure 4C:
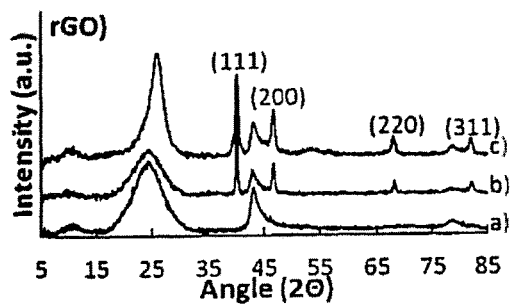
Figure 4D:
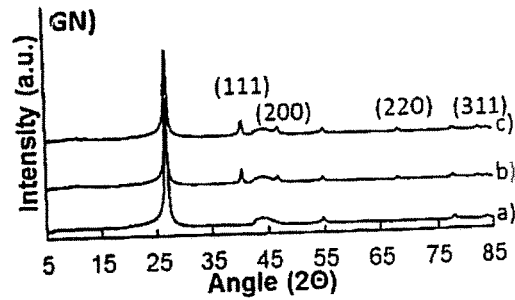

For each support, a pH shift experiment was conducted to account for pH changes resulting from support addition to an aqueous solution. Deionized water was adjusted to 12 different initial pH ($pH_i$) values using HCl or $NH_4OH$ solutions. To 15 mL of each $pH_i$ solution an appropriate amount of graphene was added and shaken for 1 hour at 100 rpm. The appropriate amount of each sample was calculated based on surface area of each support to achieve a consistent surface loading of 500 $m^2$/L for all samples. For GO, the MB surface area was used in place of the SA determined by BET. After shaking, the final pH ($pH_f$) was measured. The results are shown in FIG. 1B.

2.3 Preparation of Strong Electrostatic Adsorption—Microwave (SEA-MW) Catalysts
2.3.1 Determining Maximum Pd Uptake Conditions The pH conditions for maximum palladium uptake were found for each support and $H_2PdCl_4$ or $Pd(NH_3)_4Cl_2$ precursors. To accomplish this 50 mL of 150 ppm Pd solution of either $H_2PdCl_4$ or $Pd(NH_3)_4Cl_2$ precursor were adjusted to a range of initial pH ($pH_i$) values using HCl or $NH_4OH$ solutions. The $pH_i$ values were chosen to obtain a suitable range of final pH ($pH_f$) values for either $H_2PdCl_4$ or $Pd(NH_3)_4 Cl_2$ using results from the pH shift experiment as basis. Samples were shaken for 1 hour to allow for precursor adsorption. Aliquots (5 mL) were taken and filtered using a 0.2 μm syringe filter to determine initial and final Pd solution concentration using inductively coupled plasma optical emission spectroscopy (ICP-OES). The difference between initial and final Pd concentrations was divided by the surface loading used to calculate palladium uptake. Palladium uptake, in units of μmol Pd adsorbed per $m^2$ of support, was used to compare metal adsorption between samples of different surface areas. Exemplary results are presented in Table 2.

TABLE 2

Palladium uptake on graphene supports.

| Pd Precursor | Support | Pd Uptake (μmol/$m^2$) | Pd Wt. % |
|---|---|---|---|
| $PdCl_4^{2-}$ | GP1-5 | 0.41 | 3.00% |
| | GO | 0.14 | 2.91% |
| | rGO | 0.83 | 2.82% |
| | GN | 0.63 | 3.13% |
| $Pd(NH_3)_4^{2+}$ | GP1-5 | 0.23 | 1.67% |
| | GO | 0.52 | 10.00% |
| | rGO | 0.73 | 2.47% |
| | GN | 0.28 | 1.40% |

2.3.2 SEA of Anionic and Cationic Pd Precursors

After the pH conditions for maximum Pd uptake were identified, larger scale (1 g) adsorption was carried out at varying volumes to obtain surface loadings of 500 $m^2$/L and 1,000 $m^2$/L for $H_2PdCl_4$ or $Pd(NH_3)_4Cl_2$ respectively. Following 1 hour of shaking, the samples were vacuum filtered, dried overnight at room temperature, and oven dried at 100° C. for 12 hours. Initial and final aliquots of the $H_2PdCl_4$ or $Pd(NH_3)_4Cl_2$ uptake solutions were measured by ICP-OES to determine the Pd uptake and Pd weight percent (wt %) of each sample. The dry samples were analyzed using XRD.

2.3.3 Temperature Programmed Reduction (TPR) Determination of Appropriate MW Reduction Temperature TPR of the unreduced samples was used to determine the appropriate reduction temperature of each precursor-support sample. The reduction temperature is specific to the precursor and support interaction. Samples were analyzed in a Micromeritics AutoChem II 2920 Analyzer equipped with a thermal conductivity detector (TCD). Dried samples were loaded in a quartz wool packed U-tube cell placed in a furnace. A 10% Hydrogen, Ar balance, gas mixture was flowed at 50 sccm while temperature was ramped at 5° C./min. Gas composition changes, assumed to result from hydrogen consumption, were recorded as changes in thermal conductivity with the temperature of peak hydrogen consumption (greatest thermal conductivity change) taken as the reduction temperature.

2.3.4 Solventless Microwave Reduction

A naming system was used to denote which Pd precursor was used in each SEA-MW catalyst. The SEA of $PdCl_4^{2-}$ or $Pd(NH_3)_4^{2+}$ prior to microwave irradiation are referred to as $PdCl_4^{2-}$-GP1-5 or $Pd(NH_3)_4^{2+}$-GP1-5. SEA-MW catalysts synthesized from $PdCl_4^{2-}$ end with "A" and from Pd $(NH_3)_4^{2+}$ end with "B". For example, Pd-GP1-5_A and Pd-GP1-5_B refer to SEA-MW catalyst synthesized from $PdCl_4^{2-}$ or $Pd(NH_3)_4^{2+}$ respectively.

The dry Pd precursor loaded support samples were reduced by the solventless microwave method in a CEM Discover®-Microwave Synthesizer. The microwave program was set to a specified temperature, determined by TPR, with maximum allowed power of 200 W for 10 minutes with stirring.

2.4 SEA-MW Catalyst Characterization

The SEA-MW catalysts were characterized using XRD, XPS, TEM, and pulse chemisorption. Powder x-ray diffraction (XRD) patterns were obtained on a PANalytical MPD X'Pert Pro. XRD samples were scanned from 5 to 85° 2theta (Cu Kα x-ray source). The Scherer equation was used to calculate the crystallite size from peak broadening of diffraction peaks.

Quantitative chemical analysis of chemical states was investigated with XPS using a ThermoFisher ESCALAB 250. Survey and high-resolution photoelectron spectra were recorded with 1 eV and 0.1 eV steps, respectively. CASA-XPS 2.3 16 V software and NIST Standard Reference Database 20, Version 4.1 were used to analyze and fit the XPS spectra.

TEM imaging was performed on a FEI Titan F30 S-TWIN platform STEM system with Schottkey field emitter operating at 300 kV and images were obtained with a 16 M pixel Gatan Oneview camera. Images were analyzed using ImageJ software to measure the size and determine size distribution of samples. Pulse chemisorption experiments with $H_2$ titration were also carried out with the Micromeritics AutoChem II 2920 chemisorption analyzer to determine number of active sites, metal dispersion, metallic surface area, and active particle size. For a pulse chemisorption experiment the sample was first pretreated, to reduce all Pd sites, with flowing 10% $H_2$/Ar balance for 1 hour at 200° C. followed by a purge step using Ar flow for 30 minutes at 200° C. The sample was allowed to cool to 40° C. under Ar flow. Next, oxygen was adsorbed on surface metal sites with flowing 10% $O_2$/He balance for 30 minutes and then purged for 30 minutes with flowing Ar. Oxygen adsorption stoichiometry was assumed to be one atom of oxygen to a surface Pd site. After purging, the loop was filled with a calibrated amount of 10% $H_2$/Ar and dosed every 4 minutes over the sample, titrating the adsorbed oxygen with the hydrogen producing water and chemisorbed hydrogen. Hydrogen consumption was determined using TCD measurements recorded every 0.1 seconds. Overall stoichiometry of Pd surface site to Hydrogen consumed is 0.667Pd:1$H_2$.

2.5 General Procedure for Suzuki Reaction

Initial catalytic testing was performed using a Suzuki reaction involving 4-bromotoluene and phenylboronic acid to form 4-methyl-1,1'-biphenyl. The amount of each catalyst was normalized to 0.005 mol % of Pd relative to mols of 4-bromotoluene. The reaction was carried out at 80° C. with magnetic stirring at 500 rpm and aliquots were taken at 5, 15, 30, and 60 minutes. A small aliquot (100 μL) of the reaction was diluted in 1 mL of dichloromethane and filtered with a 0.2 μm syringe filter. Diluted samples were then analyzed using Agilent 7890B gas chromatograph system with 5977A mass spectrometry detector (GCMS).

3 Results and Discussion 3.1 Preparation of SEA-MW Catalysts

GP1-5, GO, rGO, and GN supports represent four different forms of graphene that are commonly utilized as pristine graphene alternatives to overcome cost or production issues. They have different surface areas and microporous structures, but have very similar PZC values (PZC=2.96-3.75), as shown in Table 3. Based on the similar PZC it is unsurprising that the four supports also have similar pH values at which maximum SEA occurs for tetrachloropalladate (II) anions ($PdCl_4^{2-}$) and tetraamminepalladium(II) cations (Pd $(NH_3)_4^{2+}$) (Table 3). Table 3 lists the microwave temperatures selected based on TPR results of SEA uptake of $PdCl_4^{2-}$ and $Pd(NH_3)_4^{2+}$ for each support. A representative TPR graph and microwave heating profiles for Pd-GN_B (naming system detailed in section 2.3.4) are shown in FIGS. 2 and 3A-C.

TABLE 3

SEA pH conditions for Pd complex uptake and solventless microwave reduction conditions.

| Pd Complex | Support | pH | Microwave Temperature (° C.) | Microwave Time (min) |
|---|---|---|---|---|
| A ($PdCl_4^{2-}$) | GP1-5 | 3.1 | 160 | 10 |
| | GO | 3.6 | 125 | 10 |
| | rGO | 2.9 | 155 | 10 |
| | GN | 3.1 | 135 | 10 |
| B ($Pd(NH_3)_4^{2+}$) | GP1-5 | 10.8 | 110 | 10 |
| | GO | 9.8 | 125 | 10 |
| | rGO | 11.2 | 155 | 10 |
| | GN | 10.7 | 135 | 10 |

Controlled microwave temperature for 10 minutes with maximum allowed power of (200 W) and was chosen to limit the amount of nanoparticle growth while still facilitating the simultaneous formation of Pd-defect sites in graphene. Defect sites are thought to be formed primarily by microwave irradiation being strongly absorbed by palladium resulting in very localized heating of the palladium to temperatures that can effectively pyrolyze a defect site in graphene materials. Additionally, defects have been reported to form by graphene absorbing microwave irradiation as indicated by loss of carbon as CO or $CO_2$[22]. This second mechanism can be extrapolated to Pd that is electrostatically adsorbed on oxygen containing functional groups. When the microwave irradiation removes oxygen and the basal plane carbon rearranges, a defect or Stone-Wales defect site can form and Pd that is simultaneously undergoing nucleation and growth will preferential stabilize in or on the defect site [17, 18, 28, 29].

Summaries of microwave reaction conditions are shown in Table 4.

TABLE 4

Summary of microwave irradiation reaction conditions.

| Pd Precursor | Support | Target Temp | Avg Temp (° C.) | Max Temp (° C.) | Average Pressure (PSI) | Max Pressure (PSI) | Average Power (W) | Max Power (W) |
|---|---|---|---|---|---|---|---|---|
| $PdCl_4^{2-}$ | GP1-5 | 160 | 158 | 165 | 18.3 | 35 | 3 | 100 |
| | GO | 125 | 124 | 126 | 59.8 | 89 | 3 | 151 |
| | rGO | 155 | 160 | 196 | 8.2 | 42 | 2 | 70 |
| | GN | 135 | 134 | 151 | 0.1 | 7 | 3 | 95 |
| $Pd(NH_3)_4^{2+}$ | GP1-5 | 110 | 110 | 119 | 9.4 | 35 | 1 | 78 |
| | GO | 125 | 124 | 131 | 61.9 | 94 | 3 | 200 |
| | rGO | 155 | 159 | 191 | 3.3 | 18 | 2 | 84 |
| | GN | 135 | 134 | 143 | 0.01 | 6 | 3 | 100 |

3.2 SEA-MW Catalyst Characterization

XRD analysis was used to confirm the presence of Pd on graphene supports and to calculate an approximate crystallite size of the resulting Pd nanoparticles using Scherrer analysis. XRD of the graphene supports, $PdCl_4^{2-}$ on graphene supports, and SEA-MW Pd on graphene supports are shown in FIG. 4A-D. The graphene supports contain no crystalline palladium peaks as expected. Interestingly, XRD of $PdCl_4^{2-}$ on graphene supports prior to microwave reduction indicates the presence of crystalline Pd except for $PdCl_4^{2-}$-GO. This suggests that GP1-5, rGO, and GN supports may be spontaneously reducing $PdCl_4^{2-}$ to form Pd nanoparticles through a redox mechanism in a similar method observed by Chen, et al for GO capable of additional oxidation [26]. It has been well established that GO is more of an insulator due to the high oxygen content disrupting the conductive nature of pristine graphene [27]. Thus, the GO used in this study may be unable to undergo further oxidation in order to reduce $PdCl_4^{2-}$ to form nanoparticles without added energy. Based on the TEM images, FIG. 5A-D, the SEA-MW catalysts at low magnification contain some large nanoparticles, but at high magnification a much larger population of small nanoparticles becomes apparent.

Comparing the pulse chemisorption estimated particle size, XRD crystallite size, and TEM particle size is complicated as they represent surface, volume, and number average sizes, respectively. The measured TEM diameter can be used to calculate averages based on number ($D_n$), surface ($D_S$), and volume ($D_V$) to provide a more direct comparison to pulse chemisorption estimated particle and XRD crystallite size averages. There is a size discrepancy between pulse chemisorption estimated particle size and TEM $D_S$. It is thought that the estimated particle size is overestimated in pulse chemisorption due to carbon decoration [2] resulting in lower $H_2$ uptake and thus larger estimated particle diameters than the $D_S$ TEM surface average. Pd-rGO_A has a very large $D_S$ and $D_V$ values resulting from one 205 nm diameter nanoparticle. If this nanoparticle is removed as an outlier the $D_S$ is 11±7.8 nm and the DV is 15±11 nm.

The comparison between TEM $D_V$ and XRD crystallite size is not easy for several reasons. First, crystallite size from XRD is biased towards larger crystallite sizes due to XRD being an intensity based measurement. Second, the crystallite size from XRD does not include non-crystalline Pd clusters and therefore only crystalline Pd nanoparticles are incorporated into the measurement. Third, much larger nanoparticles can contain multiple crystallites much smaller than the particle size. For these reasons, a size comparison should be made with caution. Based on the TEM images and size distributions, ultrasmall Pd nanoparticles and Pd clusters are present in much greater numbers than the larger Pd nanoparticles (FIGS. 6A-B, 7A0B, 8A-B and 9A-B) which are not accurately reflected in the XRD crystallite size for the above-mentioned reasons. Also, see Table 5.

TABLE 5

Summary of pulse chemisorption, XRD, and TEM average sizes.

| Pd Complex | Support | TEM | | | Estimated Particle Diameter (nm) | XRD Crystallite Size (nm) |
| | | $D_n$ (nm) | $D_S$ (nm) | $D_V$ (nm) | | |
|---|---|---|---|---|---|---|
| $PdCl_4^{2-}$ | GP1-5 | 9.5 ± 11 | 31 ± 24 | 36 ± 28 | 45 | 26.9 ± 3.5 |
| | GO | 15 ± 10 | 25 ± 14 | 27 ± 16 | 43 | 4.6 ± 0.3 |
| | rGO | 4.5 ± 3.7 | 110 ± 110 | 200 ± 190 | 48 | 15.4 ± 2.5 |
| | GN | 1.6 ± 1.2 | 4 ± 2.8 | 6.3 ± 4.9 | 16 | 21.3 ± 4.1 |
| $Pd(NH_3)_4^{2+}$ | GP1-5 | 2.5 ± 2.6 | 14 ± 11 | 21 ± 18 | 40 | 9.0 ± 0.7 |
| | GO | 2.6 ± 3.7 | 14 ± 12 | 16 ± 14 | 39 | 8.0 ± 0.9 |
| | rGO | 3.7 ± 1.9 | 4.4 ± 1.4 | 4.7 ± 1.6 | 36 | 4.0 ± 0.9 |
| | GN | 2.3 ± 0.8 | 2.7 ± 0.88 | 2.9 ± 0.96 | 6.3 | 4.3 ± 0.4 |

After microwave reduction, the remaining $PdCl_4^{2-}$ is reduced. Additionally, the carbon (002) peak at approximately 25° 2Θ shifts approximately 2.0° 2Θ for the GP1-5, GO, and rGO supports. This peak shift and broadening is thought to be due to the microwave irradiation which results in the removal of intercalated water and oxygen functional groups, a reduction of the long-range order of graphene, and a reduction in their flat sheet geometry. For GO the near complete disappearance of the carbon (001) peak and appearance of the carbon (002) peak following microwave irradiation is a clear indication of removal or reduction of oxygen functional groups.

The XRD results of the Pd(NH$_3$)$_4$$^{2+}$ on graphene supports, FIG. 10A-D, before microwave reduction show no presence of crystalline Pd for all 4 graphene supports. The same carbon (002) peak shifting is seen for GP1-5, GO, and rGO, as well as the near complete removal of carbon (001) in Pd-GO_B. The appearance of crystalline Pd is only seen after microwave irradiation.

All PdCl$_4$$^{2-}$ and Pd(NH$_3$)$_4$$^{2+}$ samples' crystallite sizes were analyzed and are reported in Table 6. Overall, the microwave reduction of Pd(NH$_3$)$_4$$^{2+}$ results in smaller nanoparticle crystallite sizes than the microwave reduced PdCl$_4$$^{2-}$ samples with the exception of GO. This result provides supporting evidence that the MW reduction of PdCl$_4$$^{2-}$ samples is responsible for the population of small Pd nanoparticles and that the initial spontaneous redox of PdCl$_4$$^{2-}$ with graphene results in formation of a small population of larger Pd nanoparticles. The crystallite sizes measured do not accurately represent the entire size population as XRD is an intensity measurement that is heavily biased towards larger particles.

sites [17]. 2) By controlling the pH, the oxygen functional groups can be protonated or deprotonated and electrostatically adsorb PdCl$_4$$^{2-}$ or Pd(NH$_3$)$_4$$^{2+}$, respectively. Upon microwave irradiation, these oxygen functional groups are removed and the remaining Pd will localize in or on the defect site effectively preventing carbon rearrangement to a more ordered basal plane of carbon. 3) Microwave irradiation of PdCl$_4$$^{2-}$ electrostatically adsorbed on protonated pi bonds of aromatic rings within the basal plane of graphene. Protonated pi bonds of aromatic rings can form when the basal plane of carbon is treated with HCl [14, 30]. There is a greater probability of this occurring on graphene with less oxygen content and a larger basal plane domain [30]. The microwave irradiation, in this scenario, results in forming Pd nanoparticles reaching exceptionally high temperatures that pyrolyze graphene creating Pd-defect sites.

The SEA-MW catalysts were also characterized by pulse chemisorption with H$_2$ titration to calculate the number of active sites/g, metal dispersion percentage, and estimated particle size. The results are summarized in Table 6. It is important to calculate the number of active sites/g catalyst so that a more accurate comparison of intrinsic catalytic activity can be conducted between solid supported catalysts

TABLE 6

Characterization summary of Pd-graphene catalysts synthesized by the SEA-MW method

| | | | Pulse Chemisorption | | | | |
|---|---|---|---|---|---|---|---|
| Pd Complex | Support | Pd wt loading (%) | Ns (# of active sites/g sample) | Metal Dispersion | Estimated Particle diameter (nm) | XRD crystallite size (nm) | TEM particle size (nm) |
| A (PdCl$_4$$^{2-}$) | GP1-5 | 3.0% | 4.2 × 10$^{18}$ | 2.5% | 45 | 26.9 ± 3.5 | 9.5 ± 11 |
| | GO | 2.9% | 4.3 × 10$^{18}$ | 2.6% | 43 | 4.6 ± 0.3 | 15 ± 10 |
| | rGO | 2.8% | 3.7 × 10$^{18}$ | 2.3% | 48 | 15.4 ± 2.5 | 4.5 ± 3.7 |
| | GN | 3.1% | 1.3 × 10$^{19}$ | 7.2% | 16 | 21.3 ± 4.1 | 1.6 ± 1.2 |
| B (Pd(NH$_3$)$_4$$^{2+}$) | GP1-5 | 1.7% | 2.7 × 10$^{18}$ | 2.8% | 40 | 9.0 ± 0.7 | 2.5 ± 2.6 |
| | GO | 10.0% | 1.6 × 10$^{19}$ | 2.9% | 39 | 8.0 ± 0.9 | 2.6 ± 3.7 |
| | rGO | 2.5% | 4.4 × 10$^{18}$ | 3.1% | 36 | 4.0 ± 0.9 | 3.7 ± 1.9 |
| | GN | 1.4% | 1.4 × 10$^{19}$ | 18% | 6.3 | 4.3 ± 0.4 | 2.3 ± 0.8 |

XPS was used to investigate changes in the graphene support at several steps during the SEA-MW method. FIG. 11A-E displays the high-resolution oxygen 1s XPS spectra and corresponding oxygen content (atomic %) for each support material, following SEA of PdCl$_4$$^{2-}$ or Pd(NH$_3$)$_4$$^{2+}$, and after SEA-MW. The uptake of PdCl$_4$$^{2-}$ or Pd(NH$_3$)$_4$$^{2+}$ did not diminish the oxygen atomic percentage, however oxygen was removed following microwave irradiation as expected. The high temperatures reached through microwave irradiation results in oxygen removal as CO, CO$_2$, or O$_2$ and thus defects can form depending on rearrangement of basal plane carbon [29, 30]. Although this phenomenon has been previously reported, higher microwave powers (700-1000 W) were utilized instead of the relatively low 75-200 W reached here [22, 23].

Based on these results, Pd bound to defect sites (Pd-defect) formed in the SEA-MW method are proposed to occur by three scenarios (FIG. 12). 1) The simplest method of Pd-defect formation is due to preexisting defects in the graphene supports electrostatically adsorbing PdCl$_4$$^{2-}$ or Pd(NH$_3$)$_4$$^{2+}$ prior to microwave irradiation. Previous computational research showed that the binding energy of Pd—C in defect sites is significantly greater than Pd—C in the defect-free basal plane, and more specifically vacancy-defect sites more strongly bind Pd than Stone-Wales defect with different Pd nanoparticle sizes and/or support materials. In general, lower H$_2$ uptake was observed for Pd-graphene catalysts synthesized from PdCl$_4$$^{2-}$ than catalysts synthesized from Pd(NH$_3$)$_4$$^{2+}$. This further suggests catalysts synthesized from PdCl$_4$$^{2-}$ consist of larger nanoparticles due to a redox reaction occurring during the SEA uptake of PdCl$_4$$^{2-}$, but not Pd(NH$_3$)$_4$$^{2+}$. The Pd metal dispersion was highest for Pd-GN_A and Pd-GN_B catalysts at 7.2% and 17.9%, respectively. The high metal dispersion is also reflected in the smallest estimated particle sizes of 16 nm and 6.3 nm for Pd-GN_A and Pd-GN_B catalysts. These results suggest that GN is supporting smaller nanoparticles than the GP1-5, GO, and rGO catalysts for both PdCl$_4$$^{2-}$ and Pd(NH$_3$)$_4$$^{2+}$ precursors.

Analyzing nanoparticle size with multiple techniques to gain a better understanding of particle size is very useful. However, care must be taken when comparing the pulse chemisorption estimated particle size, XRD crystallite size, and TEM particle size measurements as they represent size estimates using methods with different inherent assumptions and sources of error. Pulse chemisorption estimated particle size represents a surface average size and can overestimate the particle size due to possible carbon decoration [31]. Carbon decoration blocking metal sites results in underestimated H$_2$ uptake and thus overestimated particle sizes in pulse chemisorption. XRD can be used to calculate a volume based crystallite size, but it is biased towards larger crystallite sizes as it is an intensity based measurement. Furthermore, Pd clusters which are not crystalline are not detected by XRD and therefore the crystallite size does not accurately represent a sample containing both Pd clusters and crystalline nanoparticles. XRD crystallite size may also be skewed if even a few large particles containing multiple crystallites are present. TEM facilitates the direct measuring of particle size and can be used to calculate number, surface, and volume based particle averages to better compare to pulse chemisorption and XRD size averages. For the purposes of this current investigation TEM particle diameter number average is used to explain differences in catalytic activity between samples in this study.

3.3 SEA-MW Catalyst Initial Suzuki Testing

Figures 12A, 12B, 12C, 12D:
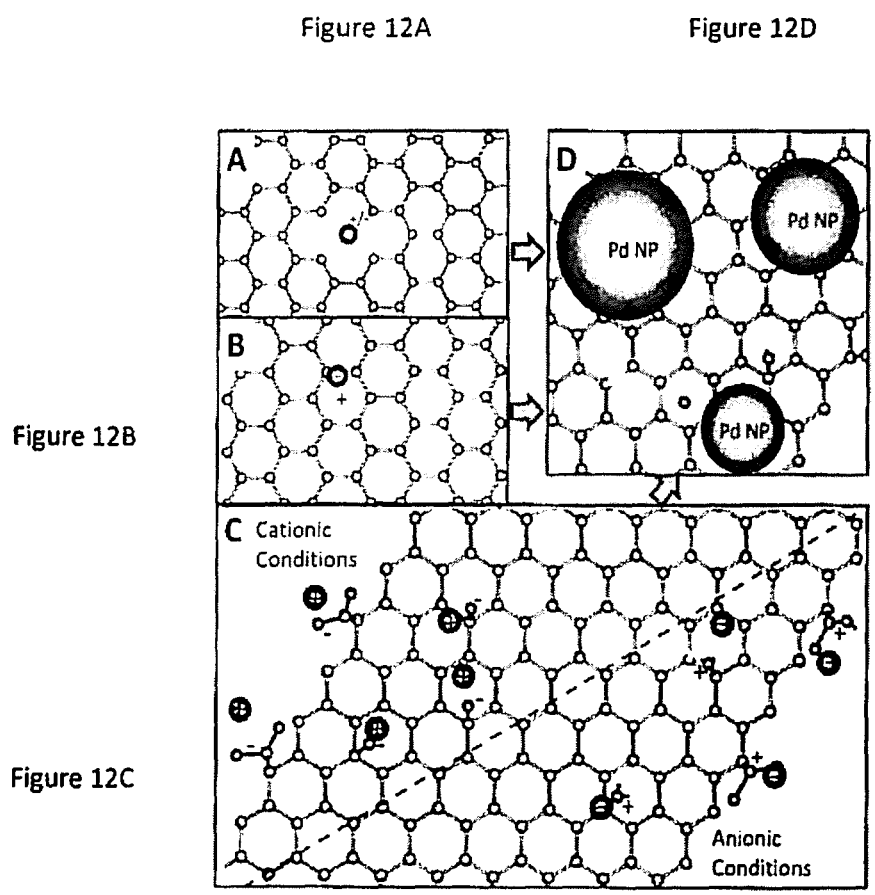
FIG. 12A-D. Proposed methods of forming palladium stabilized in or on defect sites following SEA and microwave irradiation. Three different scenarios are shown: A) Adsorption of anionic or cationic palladium to pre-existing defect sites, B) adsorption of anionic palladium to protonated pi-bonds of aromatic carbon in the basal plane away from oxygen functional groups, and C) adsorption of cationic or anionic palladium precursors to deprotonated or protonated oxygen containing functional groups. D) Palladium nanoparticles supported in or on defect sites of graphene.

One of the largest costs in Suzuki reaction processes is Pd. Therefore, developing a catalyst with increased catalytic activity which would require less total Pd is of great importance. An initial Suzuki test was conducted to compare the catalytic activity of all SEA-MW catalysts to two commercially available Pd catalysts: 10 wt % Pd-activated charcoal (Pd-AC) and 10 wt % Pd-activated carbon (Pd—C). The chosen Suzuki reaction of 4-bromotoluene and phenylboronic acid to produce 4-methyl-1,1'-biphenyl is displayed in Scheme 1. The catalysts were tested at 0.005 mol % relative to 4-bromotoluene to elucidate the most active catalyst under normalized total Pd content. FIGS. 12A and B compare $PdCl_4^{2-}$ and $Pd(NH_3)_4^{2+}$ SEA-MW catalysts to two commercially available catalysts with TOF calculated based on either total Pd mol % or active Pd mol %. Although plotting TOF vs. total Pd mol % does not properly compare catalytic activity of supported catalysts, it does provide a means to directly compare the overall cost of Pd which is often the significant cost driver. From FIG. 12A, it can be concluded that most SEA-MW catalysts are at least as active as if not exceptionally more catalytically active than Pd-AC ($2.2 \times 10^4$ hr$^{-1}$) and Pd—C ($3.1 \times 10^4$ hr$^{-1}$). Table 7 lists all catalysts TOF by mol % and active Pd mol % results.

TABLE 7

Summary of Pd catalytic activity results for exemplary Suzuki reaction

| Pd Complex | Support | Pd mol % | TOF (hr$^{-1}$) | Active Pd mol % | Active Sites TOF (hr$^{-1}$) |
|---|---|---|---|---|---|
| Commercial 10% Pd | Activated Charcoal | 0.005% | 22,009 | 0.00066% | $1.9 \times 10^5$ |
| Commercial 10% Pd | Activated Carbon | 0.005% | 31,429 | 0.00064% | $2.8 \times 10^5$ |
| $PdCl_4^{2-}$ | GP1-5 | 0.005% | 87,366 | 0.00011% | $3.8 \times 10^6$ |
| | GO | 0.005% | 25,900 | 0.00012% | $1.1 \times 10^6$ |
| | rGO | 0.005% | 30,402 | 0.00011% | $1.4 \times 10^6$ |
| | GN | 0.005% | 152,207 | 0.00034% | $2.3 \times 10^6$ |
| $Pd(NH_3)_4^{2+}$ | GP1-5 | 0.005% | 101,965 | 0.00013% | $3.9 \times 10^6$ |
| | GO | 0.005% | 116,767 | 0.00013% | $4.4 \times 10^6$ |
| | rGO | 0.005% | 12,974 | 0.00016% | $4.1 \times 10^5$ |
| | GN | 0.005% | 20,119 | 0.00081% | $1.2 \times 10^5$ |

Scheme 1. Suzuki reaction of 4-bromotoluene and phenylboronic acid.

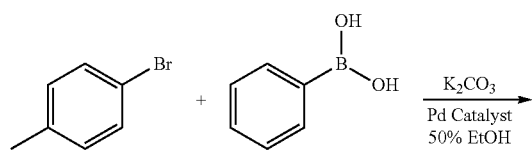

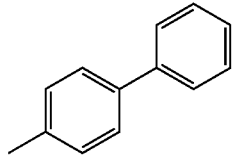

Figure 5A:
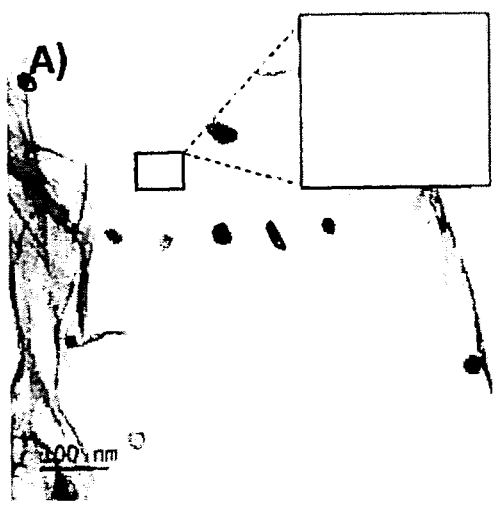
FIG. 5A-D. High Resolution Transmission Electron Microscope images of A) Pd-GO_A, B) Pd-GO_B, C) Pd-GN_A, and D) Pd-GN_B SEA-MW catalysts. Inset of A) shows zoomed in area of a palladium nanoparticle in a defect on the surface of GO. Inset of B) Higher magnification of Pd-GO_B more clearly showing both the smaller size population of 1.7±0.4 nm (68%) and larger size population 12.3±4.6 nm (32%) of palladium nanoparticles. Inset of C) Higher magnification of Pd-GN_A depicting the size distribution of 1.6±1.2 nm palladium nanoparticles. Inset of D) Higher magnification of Pd-GN_B.
Figure 5B:
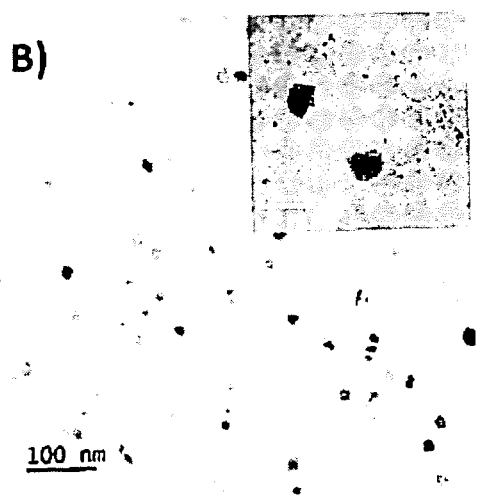
Figure 5C:
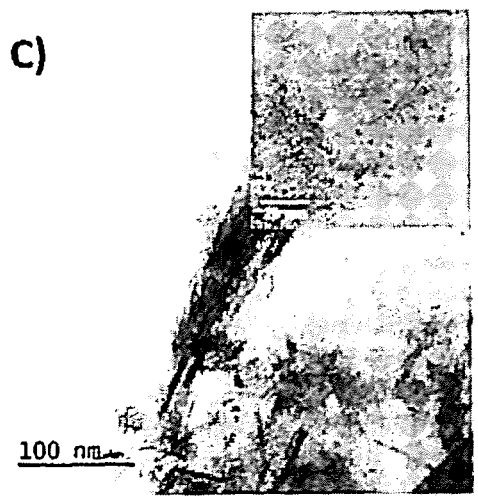
Figure 5D:
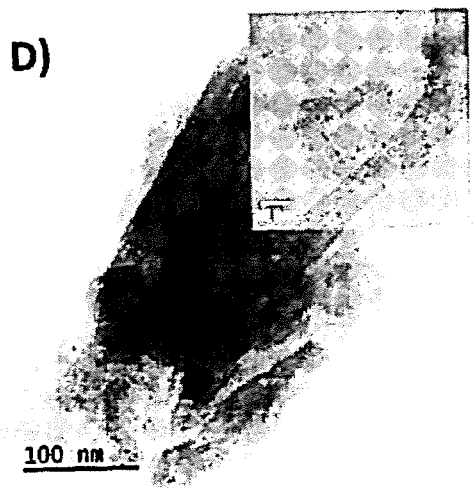
Figure 7A:
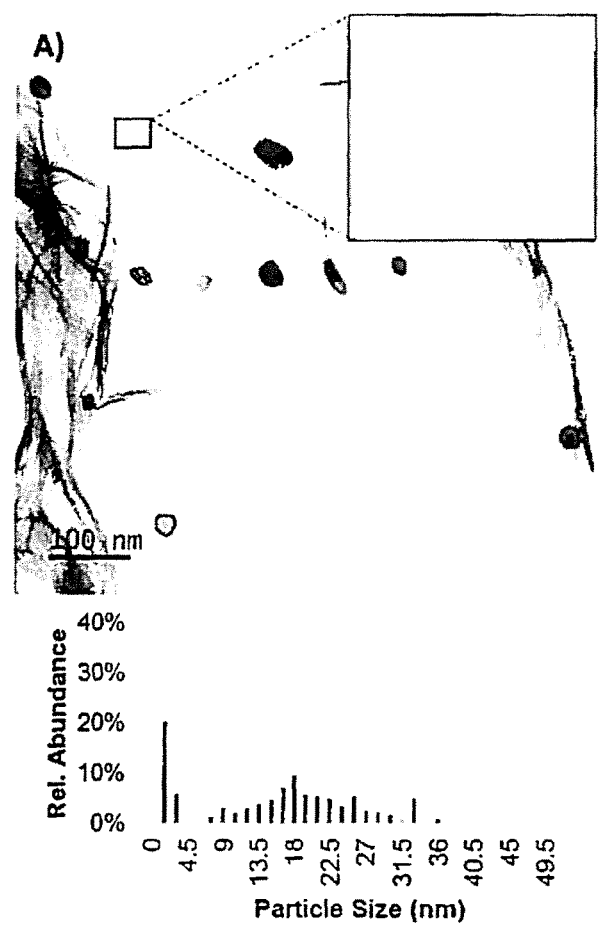
FIGS. 7A and B. High Resolution Transmission Electron Microscope images and histograms of A) Pd-GO_A and B) Pd-GO_B SEA-MW catalysts.
Figure 7B:
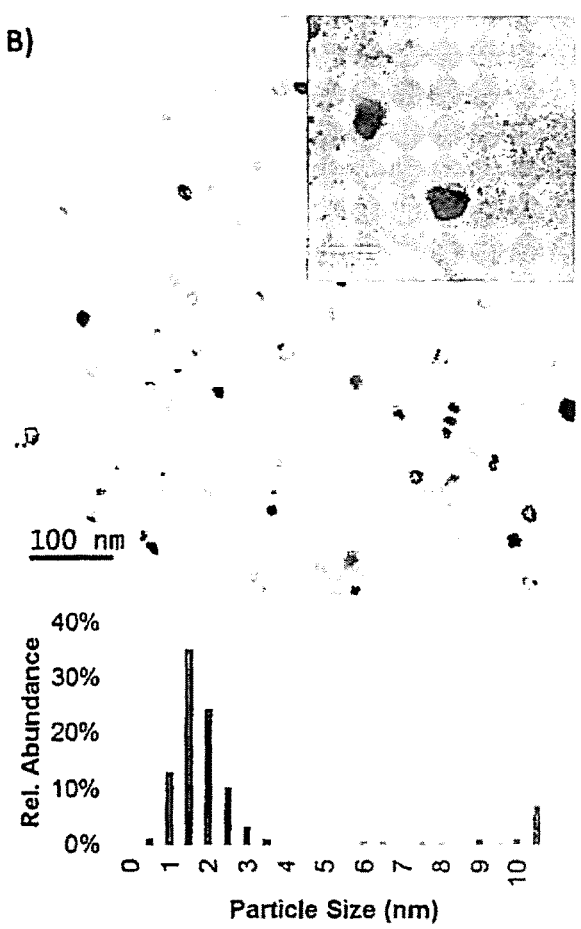
Figure 9A:
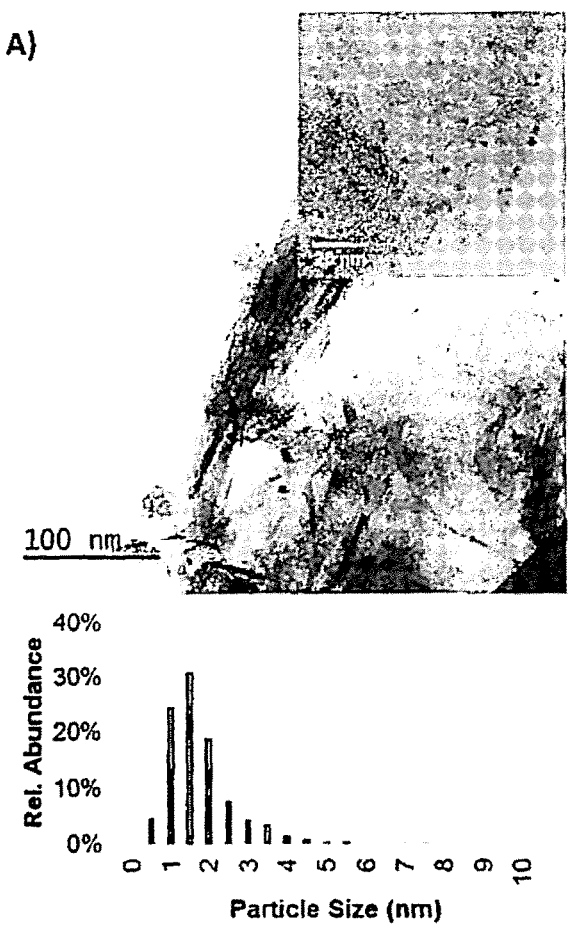
FIGS. 9A and B. High Resolution Transmission Electron Microscope images and histograms of A) Pd-GN_A and B) Pd-GN_B SEA-MW catalysts.
Figure 9B:
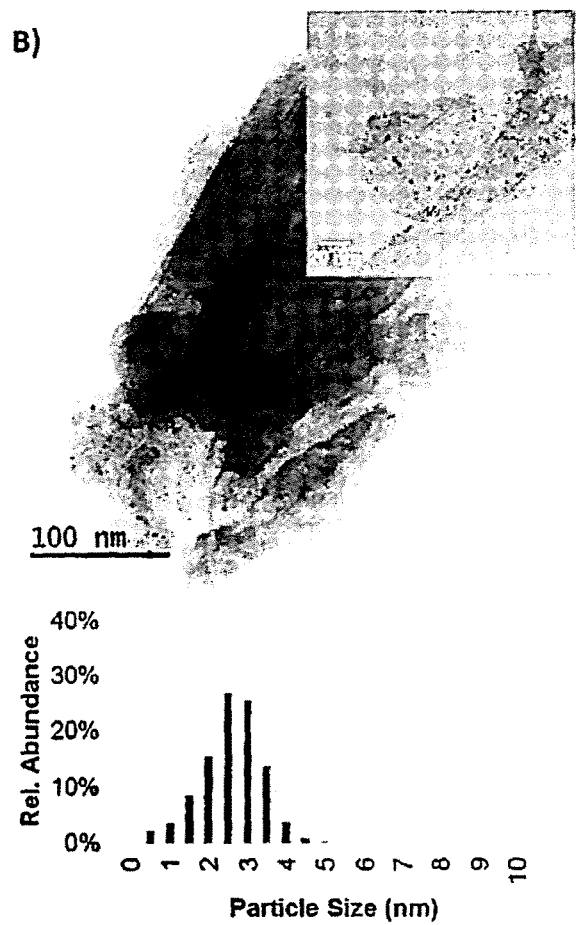
Figure 10A:
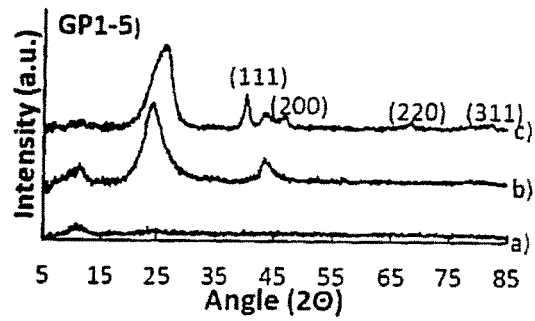
FIG. 10A-D. X-ray diffraction patterns for A, GP1-5; B, GO; C, rGO; and D, GN a) support only, b) after $Pd(NH_3)_4^{2+}$ SEA uptake, and c) after SEA-MW.
Figure 10B:
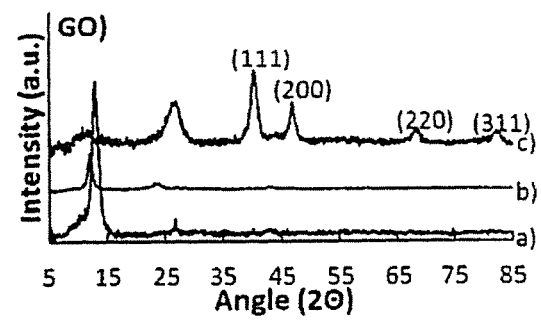
Figure 10C:
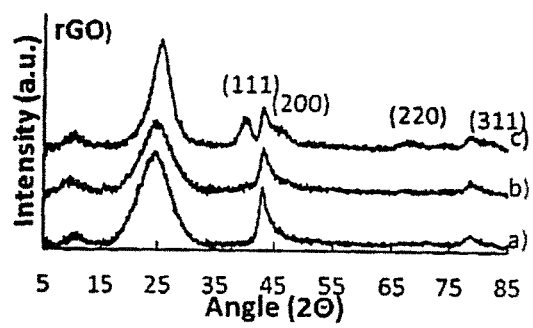
Figure 10D:
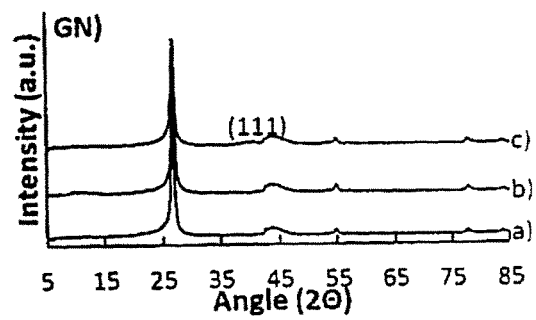
Figure 11A:
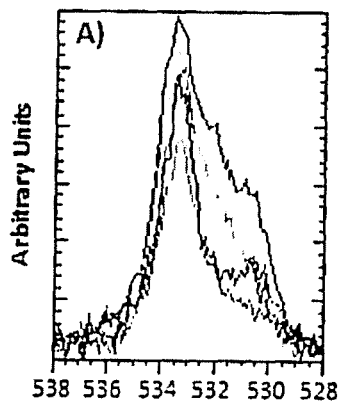
FIG. 11A-E. High resolution x-ray photoelectron spectra from the O1s region for A) GP1-5, B) GO, C) rGO, and D) GN. Within each overlaid XPS O1s spectra: the support only, following strong electrostatic adsorption with $PdCl_4^{2-}$ or $Pd(NH_3)_4^{2+}$, and after microwave irradiation of supported PdCl$_4^{2-}$ or supported Pd(NH$_3$)$_4^{2+}$. E) The corresponding quantified atomic percentage of oxygen. Oxygen content is reported for each support only (black), following strong electrostatic adsorption with PdCl$_4^{2-}$ (dark gray) or Pd(NH$_3$)$_4^{2+}$ (diagonal stripes), and after microwave irradiation of supported PdCl$_4^{2-}$ (light gray) or supported.
Figure 11B:
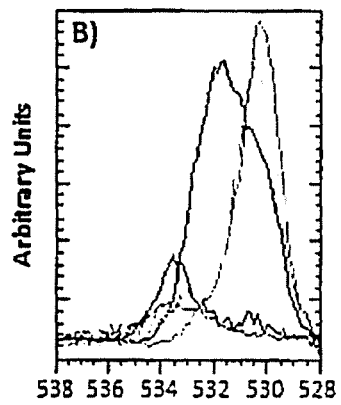
Figure 11C:
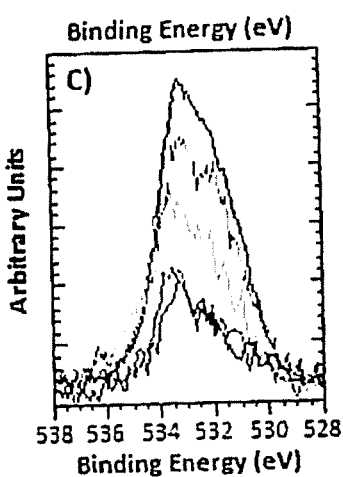
Figure 11D:
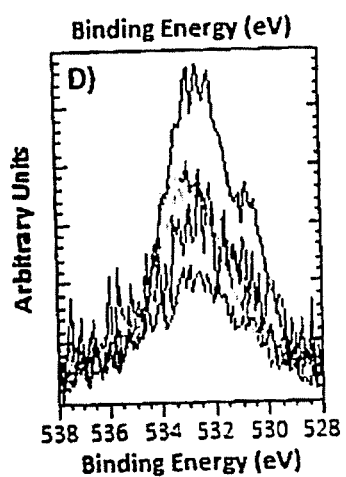
Figure 11E:
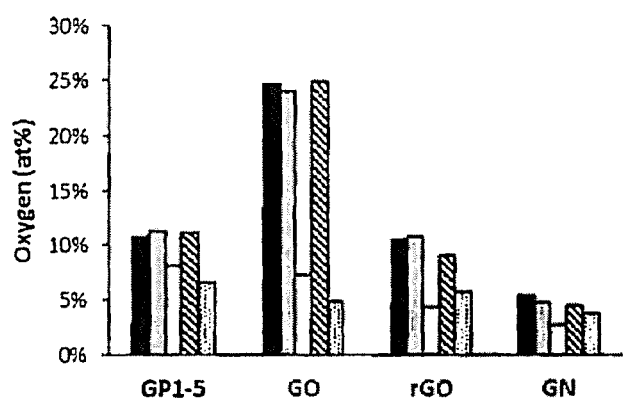

The TOF was also calculated based on active Pd mol % to more effectively compare the catalytic activities of solid supported catalysts. In FIG. 5B the SEA-MW catalysts catalytic activities (TOF=$10^6$ hr$^{-1}$) are an order of magnitude higher than commercial Pd-AC ($1.9 \times 10^5$ hr$^{-1}$) and Pd—C ($2.8 \times 10^5$ hr$^{-1}$) catalysts; except for Pd-GN_B ($1.2 \times 10^5$ hr$^{-1}$) and Pd-rGO_B ($4.1 \times 10^5$ hr$^{-1}$). By examining how defects are thought to occur the differences in favored Pd precursor for each graphene like support can be elucidated. As stated above, the SEA-MW method is thought to form Pd-defect interactions in three ways: 1) interaction with pre-existing defect sites, 2) $PdCl_4^{2-}$ or $Pd(NH_3)_4^{2+}$ SEA on protonated or deprotonated oxygen functional groups, and 3) $PdCl_4^{2-}$ SEA on protonated pi bonds of aromatic basal plane carbon. Since SEA-MW catalysts synthesized at low pH with $PdCl_4^{2-}$ are thought to utilize all three scenarios of Pd-defect formation, the differences in catalytic activities for each support can be rationalized. The Pd-GN_A and Pd-GN_B catalysts, and Pd-rGO_A and Pd-rGO_B were first analyzed as they contain similar TEM particle sizes. The large difference in catalytic activity between Pd-GN_A ($2.3 \times 10^6$ hr$^{-1}$) and Pd-GN_B ($1.2 \times 10^5$ hr$^{-1}$) catalysts is thought to be due to the low initial oxygen content of the GN support. The GN support has the lowest initial oxygen content (5.4%) of all the graphene supports tested and therefore fewer Pd-defect sites are thought to form through scenario 2 in both Pd-GN_A and Pd-GN_B. Since, Pd-GN_A is thought to form Pd-defects through all 3 scenarios, it is not surprising that it is more catalytically active as scenario 3 occurs with greater probability when graphene contains fewer oxygen groups and larger carbon basal plane domains. Likewise, the difference between Pd-rGO_A ($1.4 \times 10^6$ hr$^{-1}$) and Pd-rGO_B ($4.1 \times 10^5$ hr$^{-1}$) is less pronounced because of a greater initial oxygen content of rGO (10.5%). With more oxygen functional groups, a greater number of Pd-defects are thought to form in both Pd-rGO_A and Pd-rGO_B by scenario 2. Furthermore, only $PdCl_4^{2-}$ derived catalysts can take advantage of scenario 3 Pd-defect formation, but due to a greater oxygen content fewer Pd-defects are expected to form. SEA-MW catalysts produced from the GO support, which have an even greater initial oxygen content (24.6%), display an opposite correlation with Pd-GO_A ($1.1 \times 10^6$ hr$^{-1}$) being less catalytically active than Pd-GO_B ($4.4 \times 10^6$ hr$^{-1}$). Due to the high oxygen content and location of oxygen functional groups within the basal plane, the GO support is less likely to form Pd-defect sites through protonated pi-bonds as protonation of pi-bonds are dramatically hindered by high oxygen content, small basal plane diameters, and low density of benzenoid rings [30]. It would then be expected that the two GO catalysts would be equal in catalytic activity, however there is a large size difference between the two catalysts that makes catalytic activity comparisons difficult. The Pd-GO_A catalyst contains mainly large nanoparticles (15±10 nm), whereas the Pd-GO_B catalyst is comprised predominantly of small nanoparticles (2.6±3.7 nm). Smaller nanoparticles will have a greater number of active Pd atoms within sufficient proximity to the graphene sheet to utilize its charge donor and acceptor benefits for increased catalytic activity. Interestingly, the GP1-5 catalysts have very similar catalytic activities which can be explained by a combination of factors. First, the GP1-5 catalysts have an initial oxygen content (10.8%) that closely resembles the rGO catalysts (10.5%), which would suggest Pd-GP1-5_A being more catalytically active. Secondly, there is a size difference between the GP1-5 catalysts (Pd-GP1-5_A: 9.5±11 nm and Pd-GP1-5_B: 2.5±2.6 nm) that would favor the smaller nanoparticles of Pd-GP1-5_B being more catalytically active, similar to the rationale described for GO catalysts. Therefore, the combination of these two explanations results in similar catalytic activities between Pd-GP1-5_A ($3.8\times10^6$ hr$^{-1}$) and Pd-GP1-5_B ($3.9\times10^6$ hr$^{-1}$). Based on the trends of these results the oxygen content of a given support can be used to hypothesize whether anionic or cationic Pd precursors will provide higher catalytic activity for SEA-MW catalysts. It can also be generally concluded that higher catalytic activities are found for SEA-MW catalysts with smaller nanoparticle sizes. Considering recent advances in graphene material manufacturing, GN is very promising compared to the other graphene supports as Pd supported by GN through SEA-MW method results in a highly active catalyst that is cost effective as the metal deposition and reduction methods are simple and the support material can be produced in large quantities [32].

Conclusions

SEA and microwave irradiation have been combined to form small Pd nanoparticles stabilized in or on formed defect sites of graphene support. Pd-defect sites are thought to occur using the SEA-MW method with cationic Pd precursors by adsorption to pre-existing defect sites and deprotonated oxygen functional groups. Anionic Pd precursors form Pd-defect sites by adsorption to pre-existing defect sites, protonated oxygen functional groups, and protonated pi-bonds of aromatic carbon rings in the basal plane. Based on this, the initial oxygen content of graphene supports was found to be an excellent predictor in whether anionic or cationic Pd precursors are more likely to produce highly active catalysts for Suzuki reactions. The graphene nanoplatelet supported Pd catalyst, synthesized from anionic palladium precursors, provides ultrasmall Pd nanoparticles (1.6±1.2 nm) and a highly active catalyst with an active site TOF of $2.3\times10^6$ hr$^{-1}$ which is an order of magnitude higher than commercial catalysts (TOF=$2.8\times10^5$ hr$^{-1}$). Furthermore, the graphene nanoplatelet support costs less than $1/g, which is much more comparable to commercial carbons and charcoals than expensive graphene oxide, reduced graphene oxide, or pristine graphene materials.

REFERENCES FOR EXAMPLE 1

1. Huebner, S.; de Vries, J. G.; Farina, V. Why Does Industry Not Use Immobilized Transition Metal Complexes as Catalysts? *Advanced Synthesis & Catalysis* 2016, 358, 3-25.
2. Miyaura, N.; Suzuki, A. Palladium-Catalyzed Cross-Coupling Reactions of Organoboron Compounds. *Chem. Rev.* 1995, 95, 2457-2483.
3. Miyaura, N.; Yanagi, T.; Suzuki, A. The Palladium-Catalyzed Cross-Coupling Reaction of Phenylboronic Acid with Haloarenes in the Presence of Bases. *Synthetic Communications* 1981, 11, 513-519.
4. Ripin, D.; Bourassa, D.; Brandt, T.; Castaldi, M.; Frost, H.; Hawkins, J.; Johnson, P.; Massett, S.; Neumann, K.; Phillips, J.; Raggon, J.; Rose, P.; Rutherford, J.; Sitter, B.; Stewart, A.; Vetelino, M.; Wei, L. Evaluation of kilogramscale Sonagashira, Suzuki, and Heck coupling routes to oncology candidate CP-724,714. *Organic Process Research & Development* 2005, 9, 440-450.
5. Phan, N.; Van Der Sluys, M.; Jones, C. On the nature of the active species in palladium catalyzed Mizoroki-Heck and Suzuki-Miyaura couplings—Homogeneous or heterogeneous catalysis, a critical review. *Advanced Synthesis & Catalysis* 2006, 348, 609-679.
6. Kantchev, E. A. B.; O'Brien, C. J.; Organ, M. G. Palladium complexes of N-heterocyclic carbenes as catalysts for cross-coupling reactions—A synthetic chemist's perspective. *Angewandte Chemie-International Edition* 2007, 46, 2768-2813.
7. Oger, N.; Felpin, F. Heterogeneous Palladium Catalysts for Suzuki-Miyaura Coupling Reactions Involving Aryl Diazonium Salts. *Chemcatchem* 2016, 8, 1998-2009.
8. Fihri, A.; Bouhrara, M.; Nekoueishahraki, B.; Basset, J.; Polshettiwar, V. Nanocatalysts for Suzuki cross-coupling reactions. *Chem. Soc. Rev.* 2011, 40, 5181-5203.
9. Yin, n.; Liebscher, J. Carbon-Carbon Coupling Reactions Catalyzed by Heterogeneous Palladium Catalysts. *Chemical reviews.* 2007, 107, 133-173.
10. Polshettiwar, V.; Varma, R. S. Aqueous microwave chemistry: a clean and green synthetic tool for rapid drug discovery. *Chem. Soc. Rev.* 2008, 37, 1546-1557.
11. Polshettiwar, V.; Varma, R. S. Microwave-assisted organic synthesis and transformations using benign reaction media. *Acc. Chem. Res.* 2008, 41, 629-639.
12. Jiao, L.; Regalbuto, J. R. The synthesis of highly dispersed noble and base metals on silica via strong electrostatic adsorption: I. Amorphous silica. *Journal of Catalysis* 2008, 260, 329-341.
13. Lambert, S.; Job, N.; D'Souza, L.; Ribeiro Pereira, M. F.; Pirard, R.; Heinrichs, B.; Figueiredo, J. L.; Pirard, J.; Regalbuto, J. R. Synthesis of very highly dispersed platinum catalysts supported on carbon xerogels by the strong electrostatic adsorption method. *Journal of Catalysis* 2009, 261, 23-33.
14. Hao, X.; Barnes, S.; Regalbuto, J. R. A fundamental study of Pt impregnation of carbon: Adsorption equilibrium and particle synthesis. *Journal of Catalysis* 2011, 279, 48-65.
15. Regalbuto, J. R. Strong Electrostatic Adsorption of Metals onto Catalyst Supports. In *Catalyst Preparation: Science and Engineering*; Regalbuto, J. R., Ed.; Boca Raton: CRC Press/Taylor & Francis: Boca Raton, 2007; pp 297.
16. Dreyer, D. R.; Park, S.; Bielawski, C. W.; Ruoff, R. S. The chemistry of graphene oxide. *Chew. Soc. Rev.* 2010, 39, 228-240.
17. Yang, Y.; Castano, C. E.; Gupton, B. F.; Reber, A. C.; Khanna, S. N. A fundamental analysis of enhanced cross-coupling catalytic activity for palladium clusters on graphene supports. *Nanoscale.* 2016, 8, 19564-19572.
18. Groves, M. N.; Malardier-Jugroot, C.; Jugroot, M. Improving Platinum Catalyst Durability with a Doped Graphene Support. *Journal of Physical Chemistry C* 2012, 116, 10548-10556.
19. Felpin, F.; Ayad, T.; Mitra, S. Pd/C: An old catalyst for new applications—Its use for the Suzuki-Miyaura reaction. *European Journal of Organic Chemistry* 2006, 2679-2690.
20. Felpin, F. Ten Years of Adventures with Pd/C Catalysts: From Reductive Processes to Coupling Reactions. *Synlett* 2014, 25, 1055-1067.

21. Park, S.; Ruoff, R. S. Chemical methods for the production of graphenes. *Nature Nanotechnology* 2009, 4, 217-224.
22. Voiry, D.; Yang, J.; Kupferberg, J.; Fullon, R.; Lee, C.; Jeong, H. Y.; Shin, H. S.; Chhowalla, M. High-quality graphene via microwave reduction of solution-exfoliated graphene oxide. *Science* 2016, 353, 1413-1416.
23. Kumar, R.; Malik, S.; Mehta, B. R. Interface induced hydrogen sensing in Pd nanoparticle/graphene composite layers. *Sensors and Actuators B-Chemical* 2015, 209, 919-926.
24. McAllister, M. J.; Li, J.; Adamson, D. H.; Schniepp, H. C.; Abdala, A. A.; Liu, J.; Herrera-Alonso, M.; Milius, D. L.; Car, R.; Prud'homme, R. K.; Aksay, I. A. Single sheet functionalized graphene by oxidation and thermal expansion of graphite. *Chemistry of Materials* 2007, 19, 4396-4404.
25. Park, J.; Regalbuto, J. R. A Simple, Accurate Determination of Oxide PZC and the Strong Buffering Effect of Oxide Surfaces at Incipient Wetness. *Journal of Colloid and Interface Science* 1995, 175, 239-252.
26. Chen, X.; Wu, G.; Chen, J.; Chen, X.; Xie, Z.; Wang, X. Synthesis of "Clean" and Well-Dispersive Pd Nanoparticles with Excellent Electrocatalytic Property on Graphene Oxide. *J. Am. Chem. Soc.* 2011, 133, 3693-3695.
27. Bagri, A.; Mattevi, C.; Acik, M.; Chabal, Y. J.; Chhowalla, M.; Shenoy, V. B. Structural evolution during the reduction of chemically derived graphene oxide. *Nature Chemistry* 2010, 2, 581-587.
28. Larciprete, R.; Fabris, S.; Sun, T.; Lacovig, P.; Baraldi, A.; Lizzit, S. Dual Path Mechanism in the Thermal Reduction of Graphene Oxide. *J. Am. Chem. Soc.* 2011, 133, 17315-17321.
29. Kotakoski, J.; Krasheninnikov, A. V.; Nordlund, K. Energetics, structure, and long-range interaction of vacancy-type defects in carbon nanotubes: Atomistic simulations. *Physical Review B* 2006, 74, 245420.
30. Leon y Leon, C. A.; Solar, J. M.; Calemma, V.; Radovic, L. R. Evidence for the protonation of basal plane sites on carbon. *Carbon* 1992, 30, 797-811.
31. Tengco, J. M. M.; Lugo-Jose, Y. K.; Monnier, J. R.; Regalbuto, J. R. Chemisorption-XRD particle size discrepancy of carbon supported palladium: Carbon decoration of Pd? *Catalysis Today* 2015, 246, 9-14.
32. Dimiev, A. M.; Ceriotti, G.; Metzger, A.; Kim, N. D.; Tour, J. M. Chemical Mass Production of Graphene Nanoplatelets in similar to 100% Yield. *ACS Nano* 2016, 10, 274-279.

Example 2

Manufacture of Pt Catalysis

Figure 14:
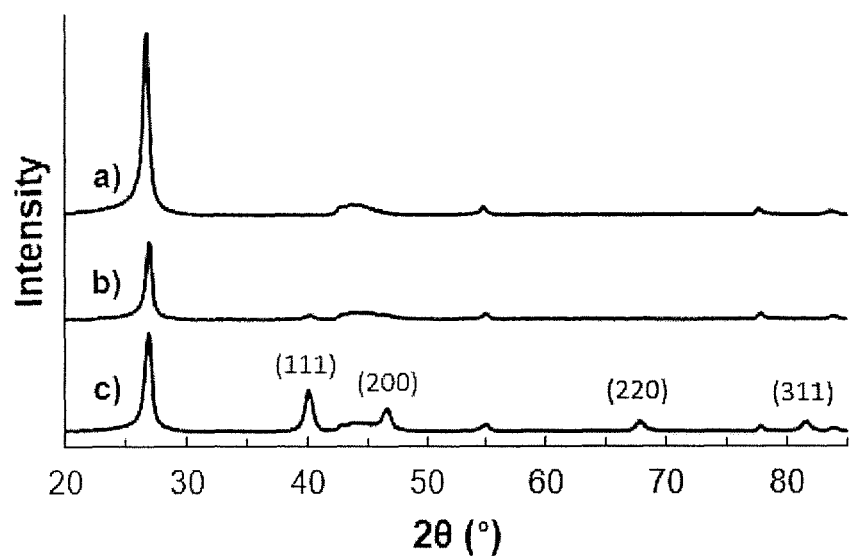
FIG. 14. X-ray diffraction pattern demonstrating the formation of a Pt on graphene nanoplatelet (GNP or GN) support. a) GNP support only, b) GNP with PtCl$_4^{2-}$ metal precursor loaded via strong electrostatic adsorption (SEA), and c) microwave irradiated Pt-GNP catalyst. The platinum crystal planes are labeled in c).

The procedures described herein (e.g. in Example 1) were used to manufacture Pt catalysts using $PtCl_4^{2-}$ as the metal precursor and graphene nanoplatelets (GNP) as the support material. Briefly, $PtCl_4^{2-}$ was deposited on graphene nanoplatelets (GNP) and the sample was then treated with an optimized set of solventless microwave irradiation conditions to facilitate the simultaneous reduction of $PtCl_4^{2-}$. This resulted in the formation of small, well-dispersed Pt nanoparticles on the GNP support and the formation of graphene defects or holes that strongly anchor the Pt nanoparticles. Exemplary results are shown in FIG. 14.

Background

While homogeneous platinum catalysts used in manufacturing often compose up to 30% of the final cost of the product, in most instances, high product viscosity typically prohibits recovery of precious metal and purification of product. This not only affects the cost structure of product preparation but also the shelf life of the product itself due to presence of the catalyst. Through the development of a solid phase catalyst, a material is provided that is more easily recoverable. This example describes an exemplary a method of manufacturing Pt catalysts to increase product quality. The Pt catalysts are effective and recyclable, and operate under mild conditions so that sensitive functionalities are preserved while performing under industrially relevant constraints (solventless, open-air).

Catalyst preparation and optimization. The work described in Example 1 (immobilizing highly active precious nanoparticles on graphene nanoplates (GNP) by strong electrostatic adsorption with solventless microwave irradiation) was expanded to synthesize a platinum-based catalyst. The SEA uptake step in the SEA-MW method provides a rational, controllable, and uniform uptake of $PtCl_4^{2-}$ metal precursor onto the surface of the GNP support. The sample is then treated with solventless microwave irradiation to facilitate the simultaneous reduction of $PtCl_4^{2-}$ to form small, well-dispersed Pt nanoparticles and to form graphene defects or holes that strongly anchor the Pt nanoparticles.

The optimal pH conditions for uptake and microwave irradiation conditions for the exemplary Pt compound $PtCl_4^{2-}$ were investigated through a pH vs. uptake study and a temperature programmed reduction (TPR) experiment, respectively. $PtCl_4^{2-}$ uptake was determined to be best at pH=3.25. Based on the TPR results, a microwave reduction temperature of 160° C. for 10 minutes was chosen. To reach and maintain a temperature of 160° C., an initial spike of microwave power of approximately 100 W for 4 seconds followed by intermittent power spikes <25 W was required. The resulting Pt-GNP catalyst was characterized using x-ray diffraction (XRD), pulse chemisorption, and transmission electron microscopy (TEM) (FIG. 14). XRD of the GNP support only and Pt-GNP catalyst confirmed the presence of crystalline Pt only in the Pt-GNP catalyst sample. Based on the Scherrer equation, the crystallite size was calculated to be 13.9±2.6 nm. Pulse chemisorption was used to determine the Pt-GNP metal dispersion and mmol of Pt active sites/g of sample. Based on TEM images, the Pt-GNP catalyst consisted of a number average nanoparticle diameter of 6.8 nm (FIG. 16B).

Catalyst evaluation. At the outset of the research, the intention was to develop a catalyst that would be attractive for implementation in large-scale commercial operations. Initial evaluations began with the solvent-free hydrosilylation of 1,1,1,3,5,5,5 heptamethyltrisiloxane (MD'M, 1) on 1-octene (2) as the model reaction. Under these conditions with low Pt loading (0.00125 mol %), the Pt catalyst described herein was able to produce quantitative conversion to the desired isomer, 3, (Scheme 2) in only 30 minutes under mild conditions (40° C.). The catalyst performed with efficiency comparable to the homogeneous industrial benchmark, Karstedt catalyst, (Pt-GNP turnover frequency (TOF)= $4.8 \times 10^6$ h$^{-1}$ and Karstedt TOF= $5.2 \times 10^6$ h$^{-1}$). The purpose of immobilizing Pt on the GNP surface was to provide enhanced activity as well as provide a means of recycling the catalyst to improve longevity. A comparison of the turnover number (TON) of the new Pt catalyst ($9.4 \times 10^6$) and the Karstedt catalyst (only $0.9 \times 10^6$) demonstrates the superiority of the new catalyst. Thus, both the activity and the stability of the new Pt-GNP catalyst system (Scheme 2) is superior.

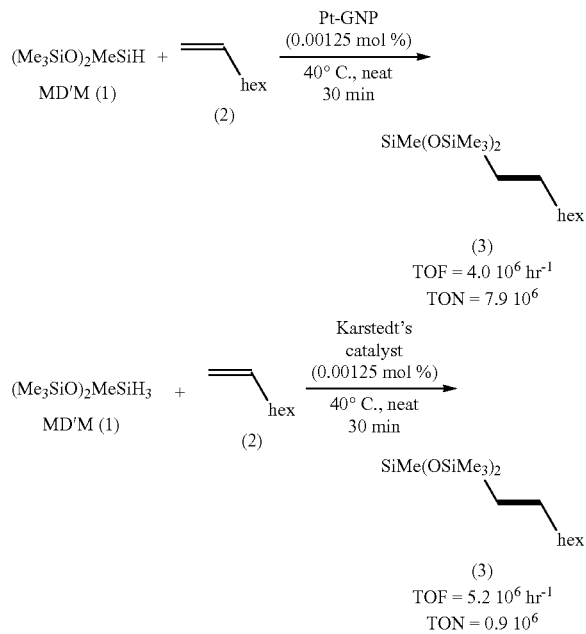

Scheme 2. Comparative evaluation of Pt-GNP hydrosilylation catalyst

Figure 15:
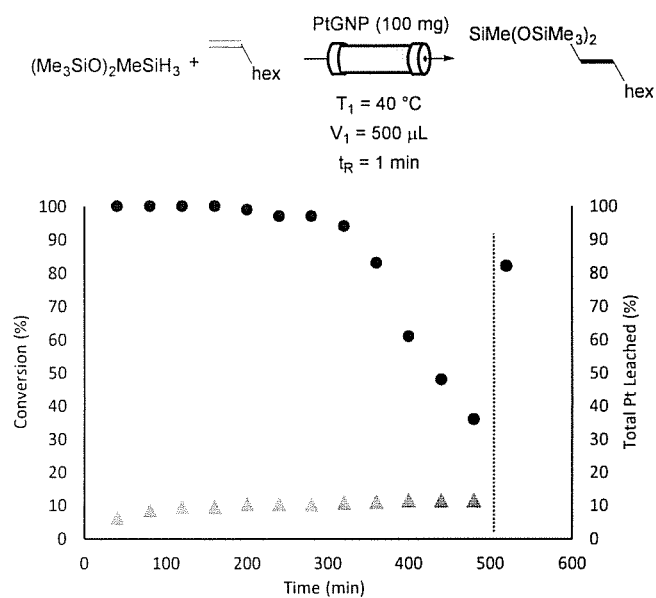
FIG. 15. Results using a packed bed reactor for the hydrosilylation of olefins. Conversion (circle) and total Pt leached (triangle) were measured before and after reinvigoration of the catalyst bed (dotted line).

The robustness and versatility of this catalyst were also measured. A longitudinal study in a continuous flow reactor to define catalyst lifetime was conducted. Using a single packed bed containing 100 mg of catalyst, a 1:1 mixture of olefin and silane was converted with a residence time of one minute to the desired product over the course of 8 hrs. This system was able to maintain >90% conversion for over 5 hrs before we observed a decrease in efficiency (36% at 8 hrs, FIG. 15). At this time, it was found that washing the catalyst bed with cyclopentyl methyl ether (CPME) restored most of the catalytic activity, producing a subsequent conversion of 80% thereafter. At this juncture, the catalyst was removed to investigate a mode of deactivation. The Pt-GNP catalyst before and after reaction was analysed with x-ray photoelectron spectroscopy (XPS, FIGS. 16A and B). High-resolution Si 2p spectra revealed an increase in Si content in the Pt-GNP after reaction sample. Based on this result, it was thought that excessive silane adsorption on the surface of the catalyst may hinder catalytic activity. Under this model, restoration of catalyst activity through silane removal by CPME was supported by high-resolution Si 2p XPS.

The catalyst exhibited minimal Pt aggregation from GNP that was insufficient to address the decrease in conversion (FIG. 17B). The extruded catalyst bed was characterized by TEM imaging to determine if particle aggregation was responsible for conversion loss. TEM analysis revealed a number average nanoparticle size of 7.0 nm (Pt-GNP before reaction=6.8 nm). This minimal increase in nanoparticle size alone could not explain the significant decrease in hydrosilylation that was observed.

Figure 17:
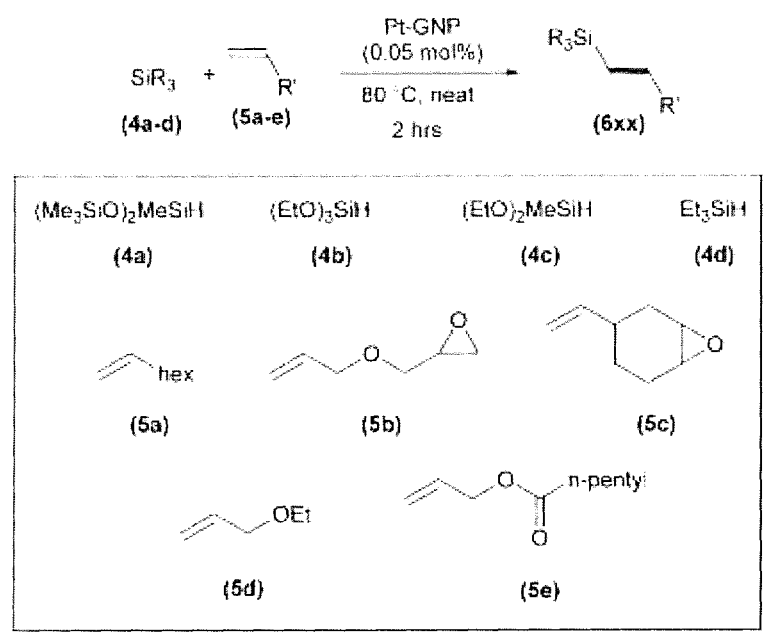
FIG. 17. Reactions for Table 8.

In order to further evaluate the industrial applicability of this system, its catalytic activity was evaluated across a gradient of silanes (4a-d) and functionalized olefins (5a-e). Many of the hydrosilylation reactions conducted in manufacturing are conducted on functionalized allyl compounds for the preparation of .gamma.-substituted propylsilanes and siloxanes. The allyl glycidyl ether (5b) and vinylcyclohexene oxide (5c) were investigated as their epoxide-containing products are numerous in the global organosilicones market as surface coatings and adhesives industries. Furthermore, many of the products manufactured in the organopolymer-modified polysiloxanes industry involve hydrosilylation of carboxylate ester-containing copolymers, which provided the impetus for the evaluation of allyl hexanoate (5e). Substrate screening was conducted under solventless conditions with 0.05 mol % of platinum at 80° C. The Pt catalyst exhibited excellent performance in mediating the hydrosilylation of these olefins by polysiloxanes, as well as tri and di-alkoxy silanes (Table 8, entries 1 and 3-7). In the case of the hydrosilylation of 5d by MD'M (Table 8 entry 3), low product yield was not accompanied with significant by-product formation. Additionally, it was found that the substrate vinylcyclohexene oxide proceeded ideally at 60° C. with MD'M as product degradation was observed at higher temperatures (Table 8, entry 2). In the case of trialkyl silane, conversions of the olefins were observed to be challenging (Table 8, entries 8 and 9). Reactions are shown in FIG. 17.

TABLE 8

Substrate scope of hydrosilylation catalyst

| Entry | Silane 4 | Olefin 5[b] | Yield (%) |
|---|---|---|---|
| 1 | a | b | 92 (6ab) |
| 2[a] |   | c | 98 (6ac) |
| 3 |   | d | 97 (6ad) |
| 4 |   | e | 54 (6ae) |
| 5 | b | a | 99 (6ba) |
| 6 |   | b | 83 (6bb) |
| 7 |   | c | 92 (6bc) |
| 8 |   | d | 99 (6bd) |
| 9 |   | e | 81 (6be) |
| 10 | c | a | 99 (6ca) |
| 11 |   | e | 86 (6ce) |
| 12 | d | a | 63 (6da) |
| 13 |   | b | 49 (6db) |
| 14 |   | d | 33 (6dd) |
| 15 |   | e | 59 (6de) |

[a]Reaction run at 60° C.
[b]5a = 2

This body of work demonstrates the successful application of a highly-active hydrosilylation catalyst that can be prepared by a relatively simple and straightforward method of preparation. This success is marked not only by its efficiency and ability to be used in continuous flow reactors, but by its operability under common industrial conditions as well as its scope of functionality to relevant substrates.

The SEA-MW method enables the preparation of other novel materials that are used in areas where catalyst depletion poses a significant economic and environmental challenge to chemical manufacturing.

While the invention has been described in terms of its several exemplary embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:
1. A method of hydrosilylating an alkene, comprising
providing a Pt catalyst, wherein the Pt catalyst is made by a method comprising
i) depositing a Pt precursor on a carbon-based material; and
ii) irradiating carbon-based material comprising deposited Pt precursor with radiant energy sufficient to attach Pt from the Pt precursor to the carbon-based material, thereby forming a Pt catalyst; and contacting the alkene with the Pt catalyst in the presence of a hydrosilylating agent, wherein the carbon-based material is a graphene-based material; and wherein the method is performed in a continuous flow reactor and further comprises a step of, at a period of time after the contacting step, washing the catalyst to remove adsorbed Si.

2. The method of claim 1, wherein the graphene-based material comprises one or more of GP1-5, graphene oxide (GO), reduced graphene oxide (rGO), graphene nanoplatelets (GN), graphene nanoplatelet aggregates, graphene nanotubes, monolayer graphene, few-layer graphene (FLG) and multilayer graphene (MLG).

3. The method of claim 1, wherein the step of depositing is performed by
loading the graphene-based material with the Pt precursor via strong electrostatic adsorption (SEA), wherein the loading takes place in an aqueous solution.

4. The method of claim 3, wherein, prior to the step of irradiating, the method further comprises the steps of:
separating graphene-based material loaded with Pt precursor from the aqueous solution; and
drying the graphene-based material loaded with Pt precursor.

5. The method of claim 3, further comprising, prior to the step of loading, the steps of determining an optimum pH for SEA of the Pt precursor to the graphene-based material and adjusting the pH of the aqueous solution to the optimum pH.

6. The method of claim 1, wherein the step of depositing is performed by dry impregnation, charge enhanced dry impregnation, wet impregnation, precipitation, co-precipitation, precipitation-impregnation or deposition precipitation.

7. The method of claim 1, wherein the radiant energy is microwave energy.

8. The method of claim 1, wherein the graphene-based material is GN.

9. The method of claim 1 wherein the Pt precursor is $PtCl_4^{2-}$.

10. The method of claim 1, wherein the step of irradiating is performed at a fixed temperature.

11. The method of claim 10, wherein the fixed temperature is 160° C.

12. The method of claim 1, wherein the alkene is 1-octene.

13. The method of claim 1, wherein the hydrosilylating agent is $(Me_3SiO)_2MeSiH$.

14. The method of claim 1, wherein the Pt catalyst comprises Pt nanoparticles that are 10 nm or less in size.

15. The method of claim 5, wherein the pH is 3.25.

16. The method of claim 1, wherein the turnover number for the reaction is $9.4 \times 10^6$.

17. The method of claim 1, wherein the period of time is at least 5 hours.

18. The method of claim 17, wherein the period of time is 8 hours.

19. The method of claim 1, wherein the hydrosilylating agent is $(Me_3SiO)_2MeSiH$, $(EtO)_3SiH$, $(EtO)_2MeSiH$ or $Et_3SiH$.

20. The method of claim 1, wherein the alkene is a functionalized allyl compound.

21. The method of claim 20, wherein the functionalized allyl compound is vinylcyclohexene oxide, 1-octene, allyl gycidal ether,

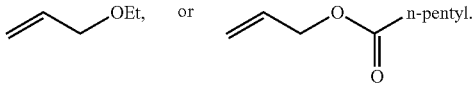

22. The method of claim 19, wherein if the hydrosilylating agent is $(EtO)_3SiH$, then the alkene is not allyl gycidal ether.

23. The method of claim 1, wherein the step of contacting produces a γ-substituted propylsilane or a siloxane.

* * * * *